United States Patent
Ocak et al.

(10) Patent No.: US 12,274,432 B2
(45) Date of Patent: Apr. 15, 2025

(54) SUTURE MEMBER, SUTURING NEEDLE AND SUTURING DEVICE

(71) Applicant: Ubbat Ocak, Porsgrunn (NO)

(72) Inventors: Ubbat Ocak, Porsgrunn (NO); Erik Pavels Petersen, Porsgrunn (NO); Martin W. Ronningen, Porsgrunn (NO)

(73) Assignee: MUB Medical Solutions AS, Skien (NO)

( * ) Notice: Subject to any disclaimer, the term of this patent is extended or adjusted under 35 U.S.C. 154(b) by 683 days.

(21) Appl. No.: 17/260,578

(22) PCT Filed: Jun. 27, 2019

(86) PCT No.: PCT/NO2019/050135
§ 371 (c)(1),
(2) Date: Jan. 15, 2021

(87) PCT Pub. No.: WO2020/017976
PCT Pub. Date: Jan. 23, 2020

(65) Prior Publication Data
US 2021/0275163 A1    Sep. 9, 2021

(30) Foreign Application Priority Data

Jul. 16, 2018  (NO) .................................. 20180994

(51) Int. Cl.
*A61B 17/04* (2006.01)
*A61B 17/06* (2006.01)

(52) U.S. Cl.
CPC .......... *A61B 17/0401* (2013.01); *A61B 17/04* (2013.01); *A61B 17/0487* (2013.01);
(Continued)

(58) Field of Classification Search
CPC ................ A61B 17/04; A61B 17/0487; A61B 17/06066; A61B 17/0401; A61B 2017/0496
See application file for complete search history.

(56) References Cited

U.S. PATENT DOCUMENTS

| 4,592,356 A * | 6/1986 | Gutierrez ........... A61B 17/3403 606/221 |
| 4,708,141 A | 11/1987 | Inoue |

(Continued)

FOREIGN PATENT DOCUMENTS

| CA | 2125839 | 1/1995 |
| CN | 202458525 | 10/2012 |

(Continued)

OTHER PUBLICATIONS

P26745INPC FER Search Report.
(Continued)

*Primary Examiner* — Darwin P Erezo
*Assistant Examiner* — Zehra Jaffri
(74) *Attorney, Agent, or Firm* — Christian D. Abel

(57) ABSTRACT

An interrupted suture member comprises a flexible elongate member, having a first end and an opposite second end, and one or more detents configured for anchoring the suture member in soft tissue. The second end comprises a movable locking member, whereby a force exerted on the tissue may be adjusted by moving the locking member along at least a portion of the suture member. A suture needle comprising a notch for grabbing and holding an interrupted suture or a suture needle being hollow and comprising a slit sufficiently wide and long for easily insertion and guiding of a suture in the suture needle. A suturing insertion device for connecting to a suturing needle consisting two handles or a suturing apparatus comprises an arcuate suturing needle rotatably arranged in an apparatus housing, a cavity for holding a (Continued)

(a)

(b)

plurality of suture members, and drive means to selectively rotate said suturing needle.

8 Claims, 19 Drawing Sheets

(52) U.S. Cl.
CPC .............................. *A61B 17/06066* (2013.01); *A61B 2017/0419* (2013.01); *A61B 2017/0445* (2013.01); *A61B 2017/0462* (2013.01); *A61B 2017/0464* (2013.01); *A61B 2017/0496* (2013.01)

(56) References Cited

U.S. PATENT DOCUMENTS

| | | | |
|---|---|---|---|
| 4,741,330 A | 5/1988 | Hayhurst | |
| 4,950,285 A * | 8/1990 | Wilk | A61B 17/06 24/17 AP |
| 5,269,809 A | 12/1993 | Hayhurst | |
| 5,643,321 A * | 7/1997 | McDevitt | F16B 13/0866 606/313 |
| 6,010,513 A | 1/2000 | Tormala | |
| 6,506,190 B1 * | 1/2003 | Walshe | A61B 17/0401 606/232 |
| 6,533,795 B1 * | 3/2003 | Tran | A61B 17/0469 606/144 |
| 6,699,255 B1 | 3/2004 | Cuschieri | |
| 8,747,483 B2 * | 6/2014 | Ginn | A61B 17/0057 623/23.72 |
| 2002/0151193 A1 | 10/2002 | Self | |
| 2004/0068292 A1 | 4/2004 | Koseki | |
| 2004/0122456 A1 * | 6/2004 | Saadat | A61B 17/3478 606/157 |
| 2005/0251208 A1 * | 11/2005 | Elmer | A61B 17/0401 606/232 |
| 2007/0173888 A1 | 7/2007 | Gertner | |
| 2008/0003346 A1 | 2/2008 | Zinti et al. | |
| 2008/0039894 A1 | 2/2008 | Catanese | |
| 2009/0248071 A1 | 10/2009 | Saint | |
| 2009/0259251 A1 | 10/2009 | Cohen | |
| 2010/0087854 A1 * | 4/2010 | Stopek | A61B 17/0057 606/215 |
| 2010/0137891 A1 | 6/2010 | Shalon | |
| 2010/0312260 A1 | 12/2010 | Herron | |
| 2011/0313431 A1 | 12/2011 | Shimko | |
| 2012/0078057 A1 * | 3/2012 | Scott | A61B 17/04 600/201 |
| 2012/0245629 A1 | 9/2012 | Gross | |
| 2012/0303059 A1 | 11/2012 | Saadat | |
| 2013/0012990 A1 | 1/2013 | McClellan | |
| 2014/0296881 A1 | 10/2014 | Ranucci | |
| 2014/0371792 A1 | 12/2014 | Beck | |
| 2016/0106421 A1 | 4/2016 | Eliach | |
| 2016/0157858 A1 | 6/2016 | Horton | |
| 2017/0265858 A1 | 9/2017 | Rosenberg | |
| 2018/0235746 A1 * | 8/2018 | Pilgeram | A61B 17/0401 |
| 2019/0014241 A1 | 5/2019 | Winter | |
| 2022/0192653 A1 | 6/2022 | Doctor et al. | |

FOREIGN PATENT DOCUMENTS

| | | | |
|---|---|---|---|
| EP | 1093758 | 1/2001 | |
| EP | 2436317 | 4/2012 | |
| JP | S54166093 | 11/1979 | |
| JP | 2005000294 | 1/2005 | |
| JP | 2008148933 | 7/2008 | |
| LV | 14892 | 8/2014 | |
| WO | 90/14795 | 12/1990 | |
| WO | 9852473 | 11/1998 | |
| WO | 2007/098212 | 8/2007 | |
| WO | 2009146387 | 3/2009 | |
| WO | 2013126748 | 8/2013 | |
| WO | 2013146220 | 10/2013 | |
| WO | 2017051409 | 3/2017 | |
| WO | WO-2018132801 A1 * | 7/2018 | A61B 17/0057 |

OTHER PUBLICATIONS

Statement of relevance for LV14892: Medical instrument comprising a hollow needle; see figure 1 and the abstract.
Norwegian Search Report of Feb. 15, 2019 in Application NO20180994, filed inter alia as a statement of relevance for any non-English references cted therein.
ISR dated Sep. 19, 2019, filed inter alia as a statement of relevance for any non-English references cted therein.
IPEA dated Apr. 30, 2020, filed inter alia as a statement of relevance for any non-English references cted therein.
IPRP dated Jun. 23, 2020, filed inter alia as a statement of relevance for any non-English references cted therein.
PCT Written Opinion dated Apr. 30, 2020.

* cited by examiner

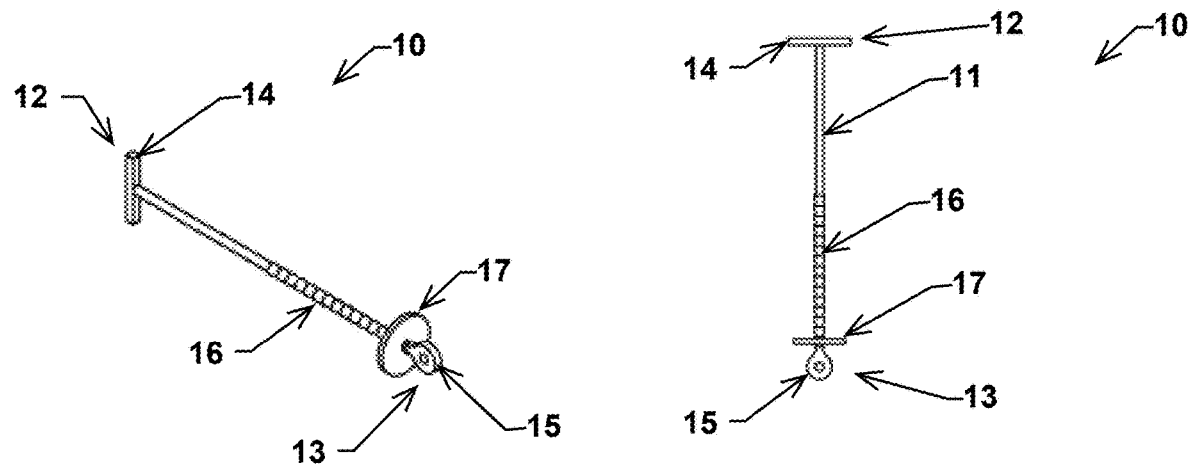
Fig. 1 (a) (b)
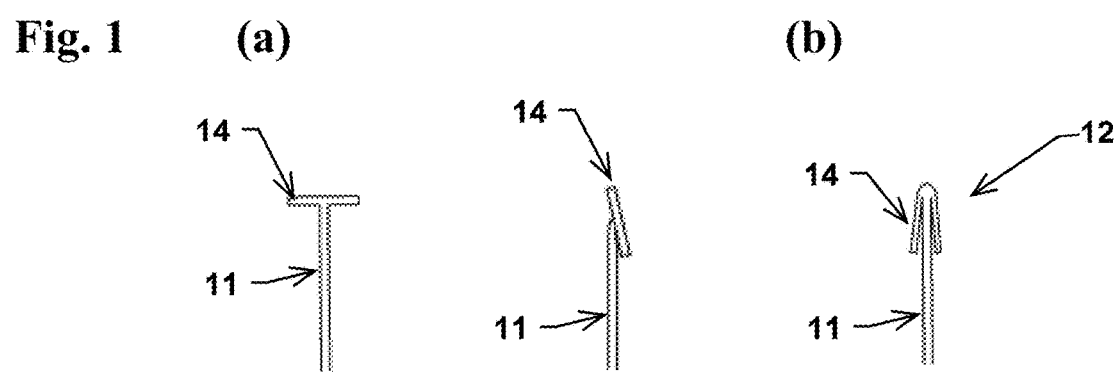
(a) (b) (c)
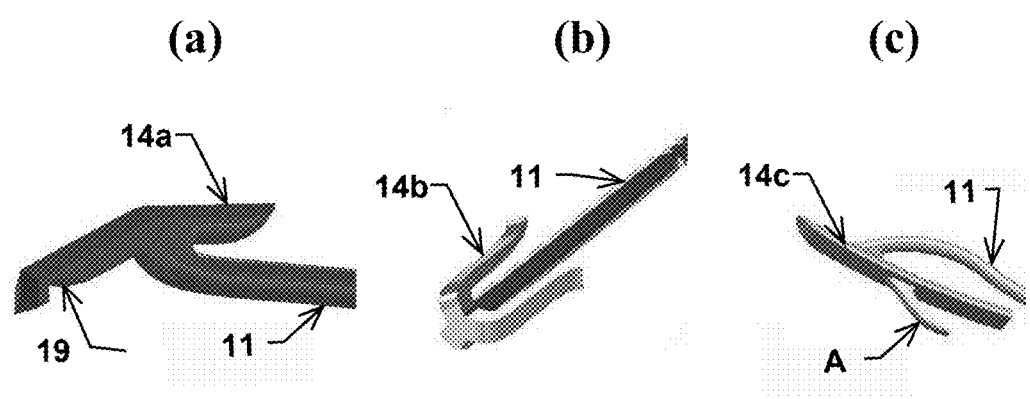
(d) (e) (f)
Fig. 2

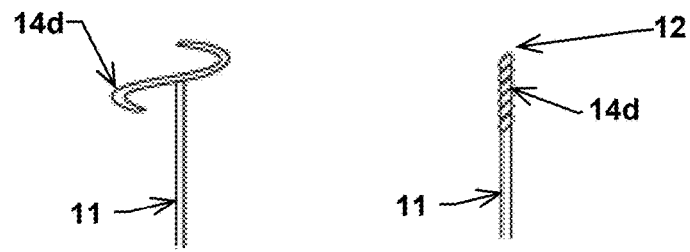
Fig. 3     (a)     (b)
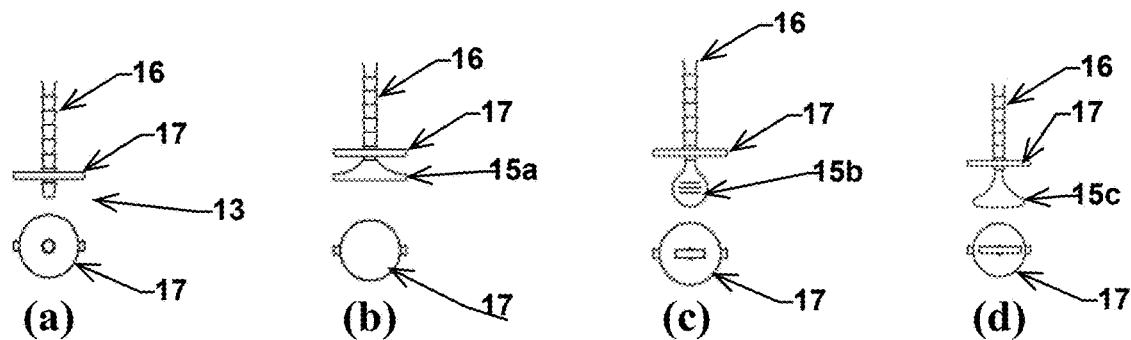
Fig. 4
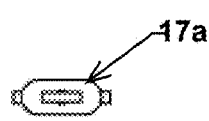     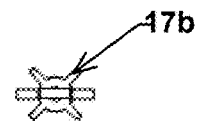
Fig. 5     (a)     (b)
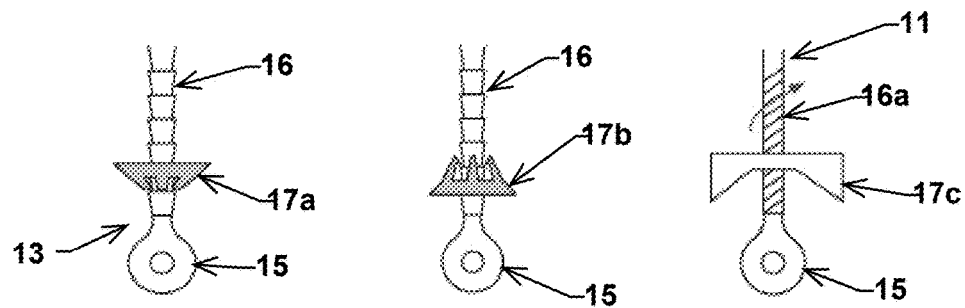
Fig. 6     (a)     (b)     (c)

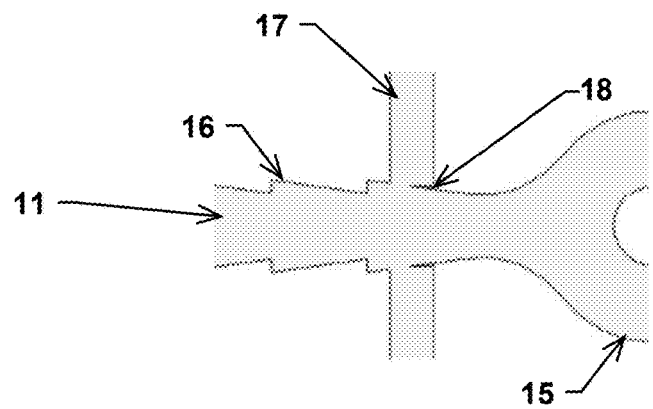
Fig. 7
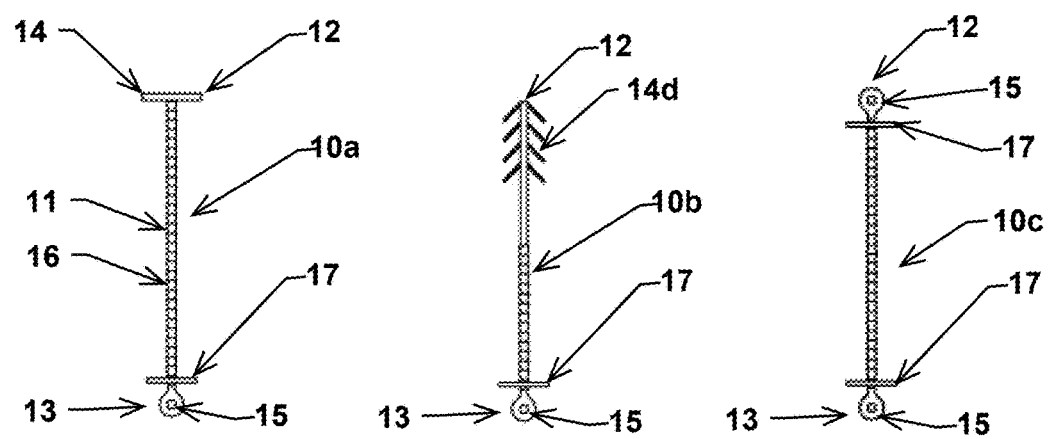
Fig. 8 (a) (b) (c)
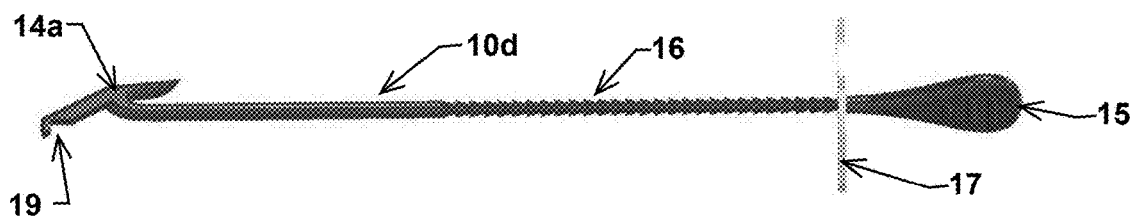
Fig. 8 (d)

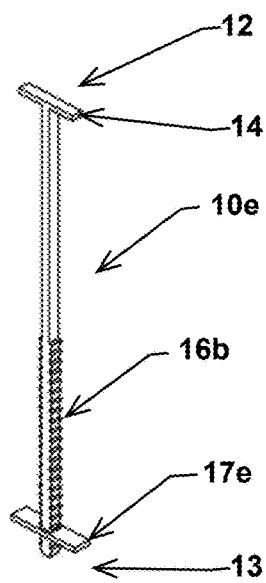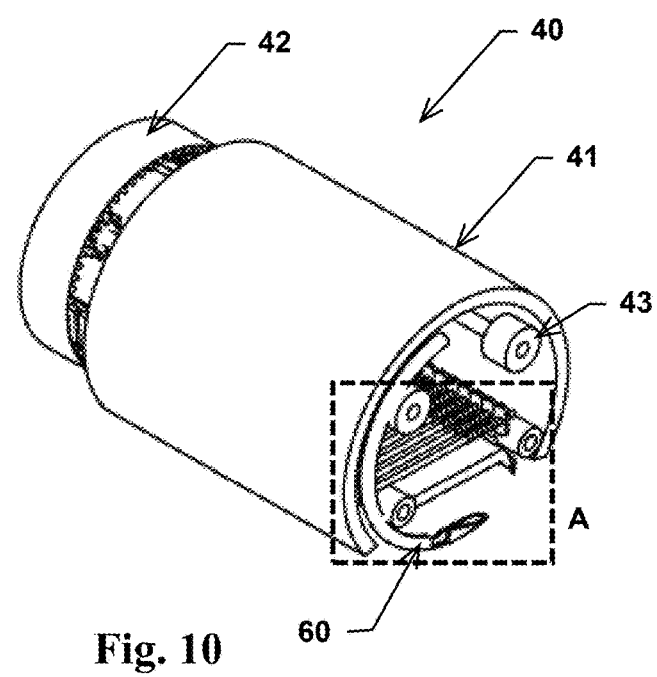
Fig. 9    Fig. 10
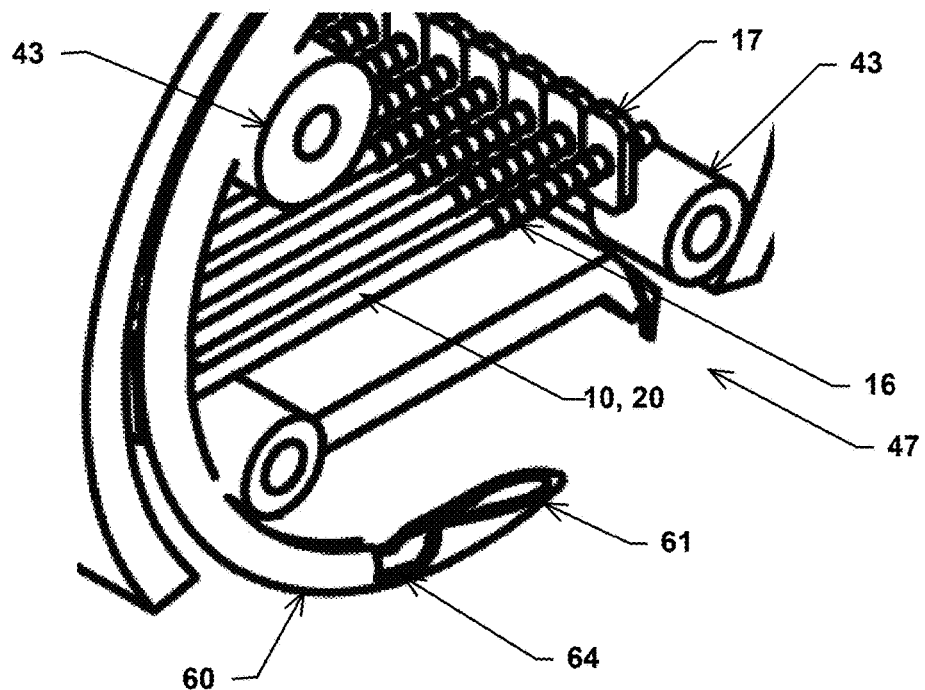
Fig. 11

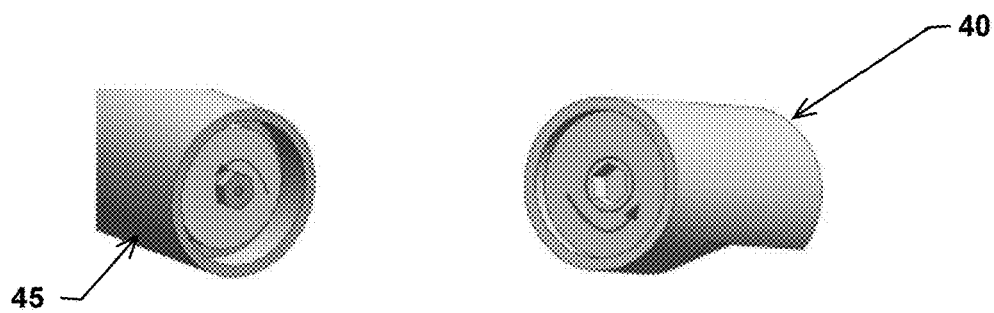
Fig. 14     (a)         (b)
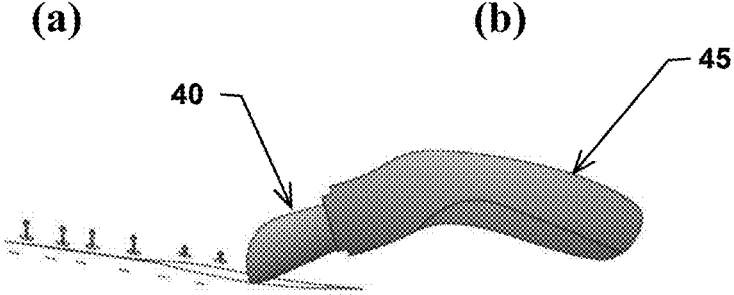
Fig. 15
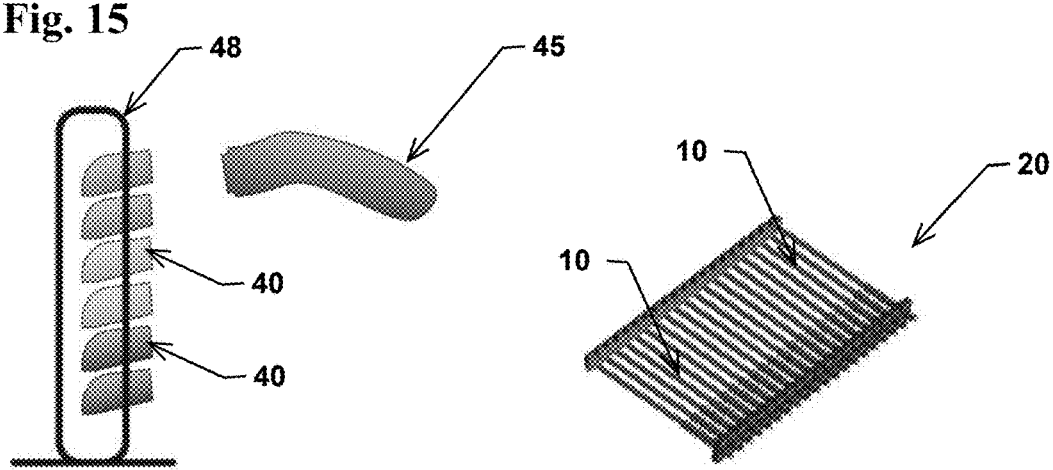
Fig. 16         Fig. 17
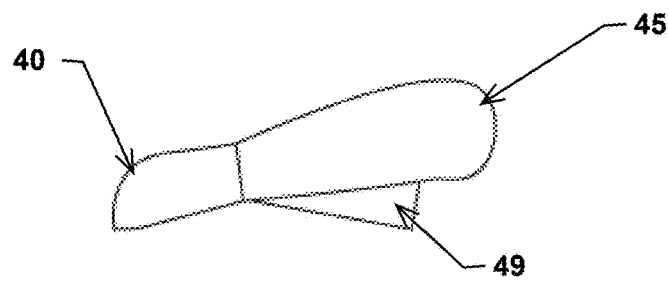
Fig. 18

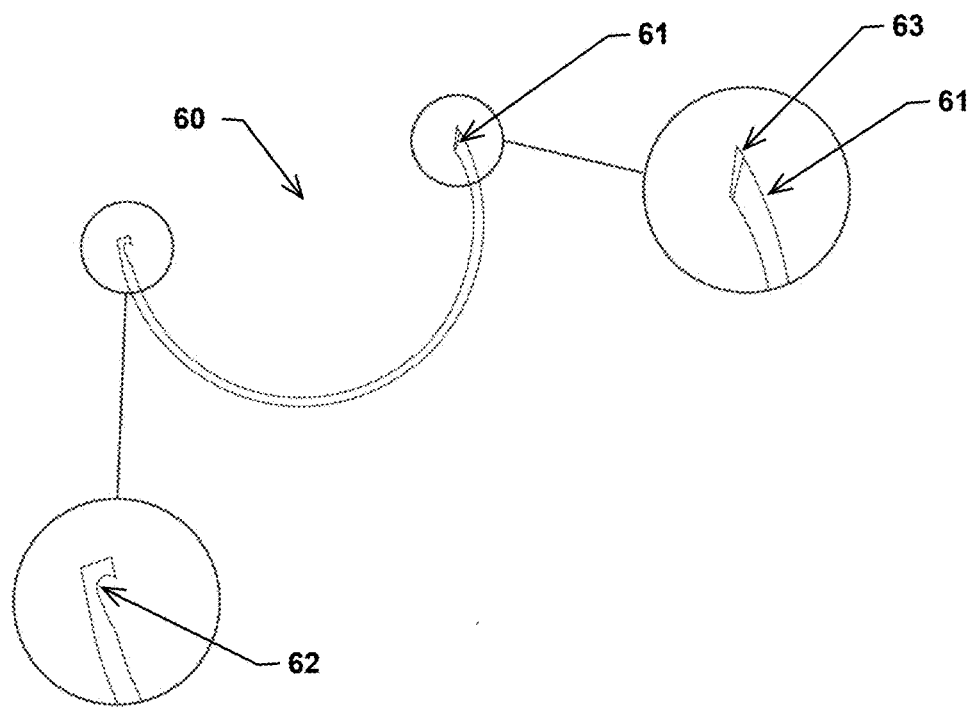
Fig. 21
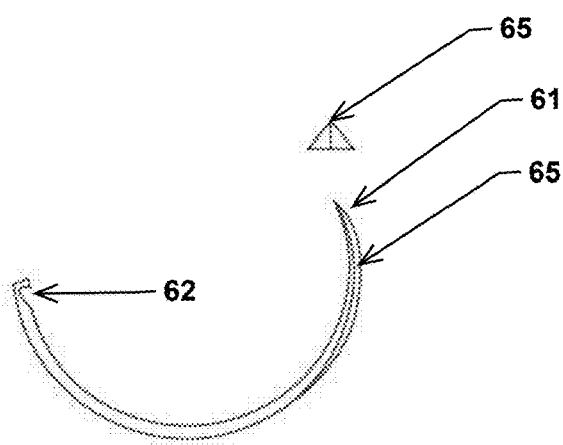
Fig. 22
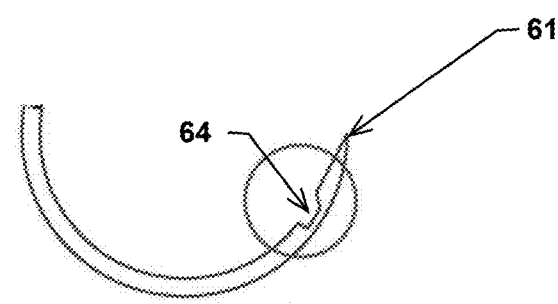
Fig. 23
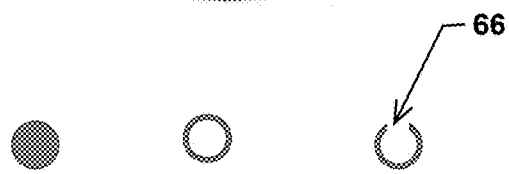
Fig. 24    (a)    (b)    (c)

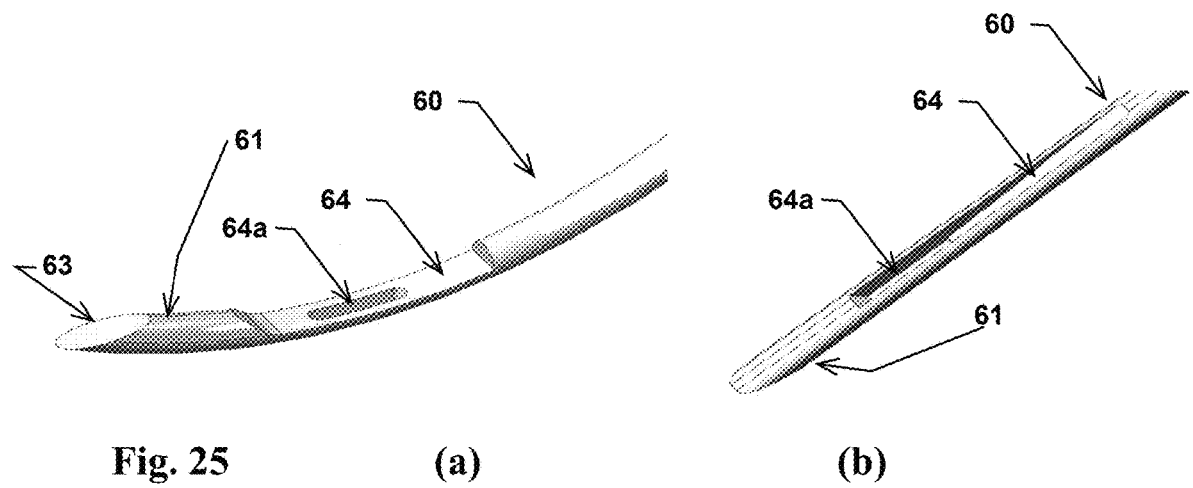
Fig. 25 (a) (b)
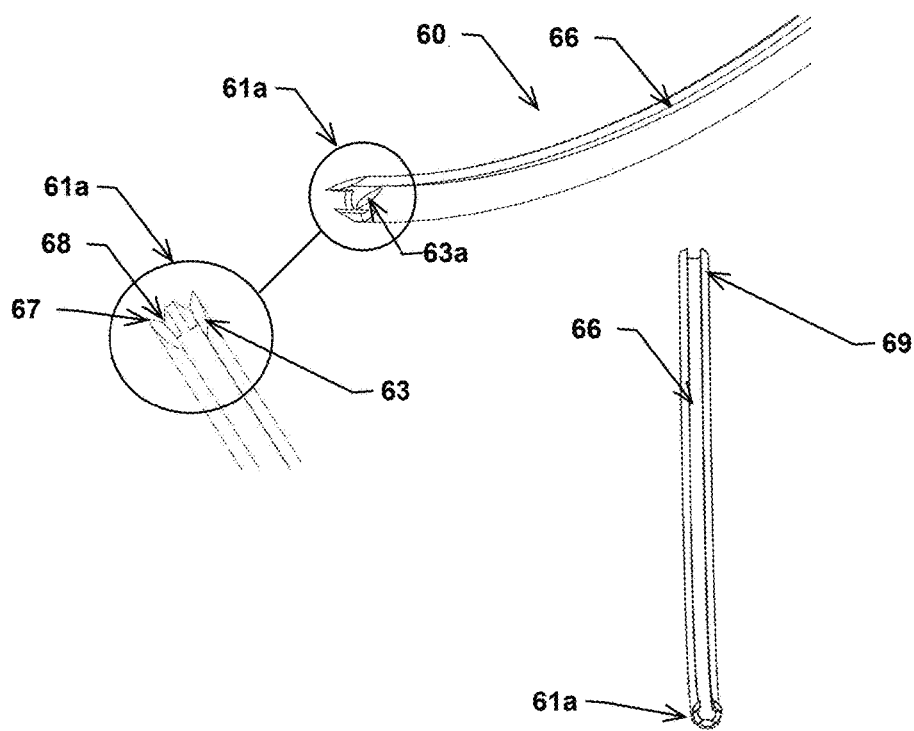
Fig. 26

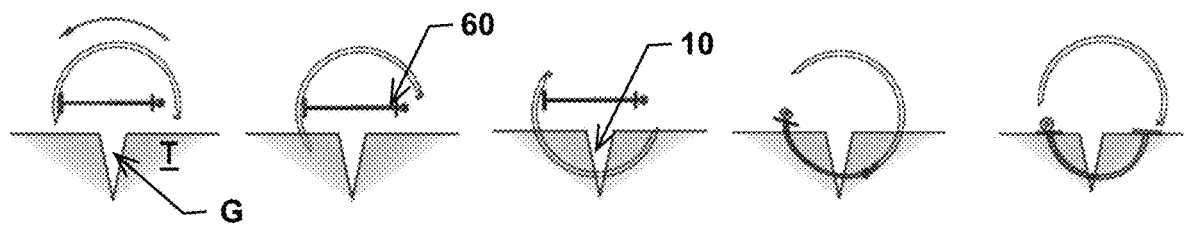
Fig. 28
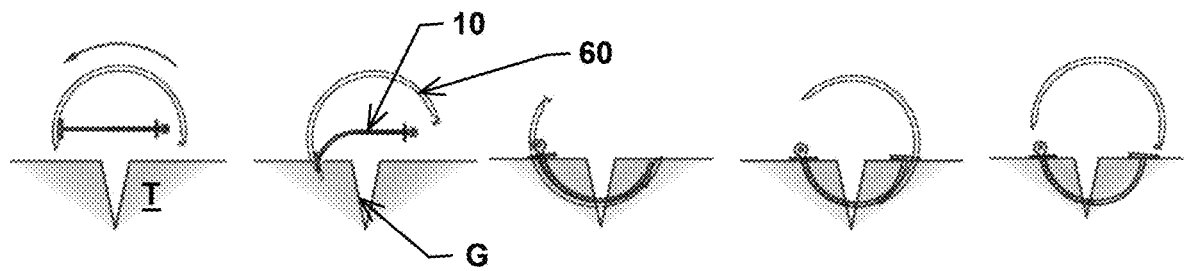
Fig. 29
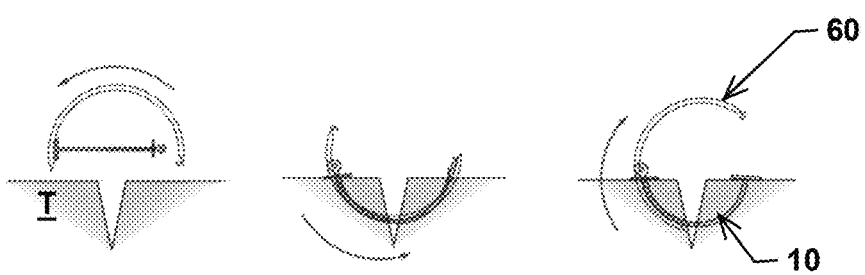
Fig. 30
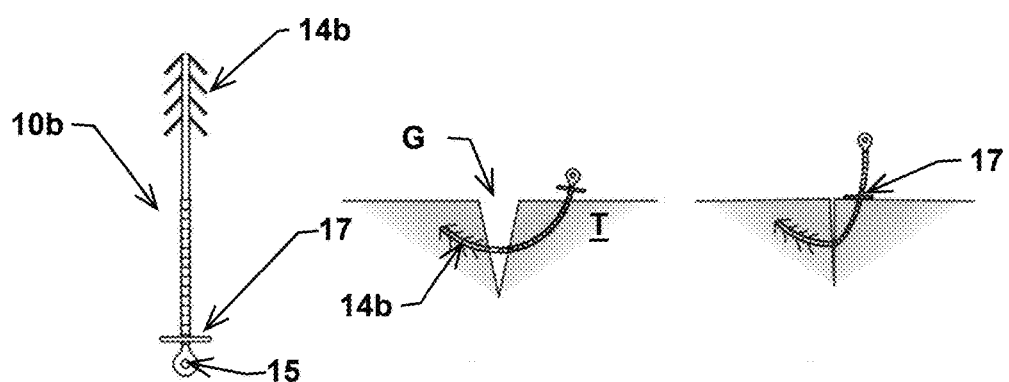
Fig. 31 (a) (b) (c)

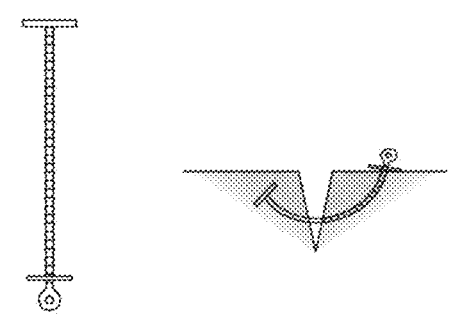
Fig. 32     (a)     (b)
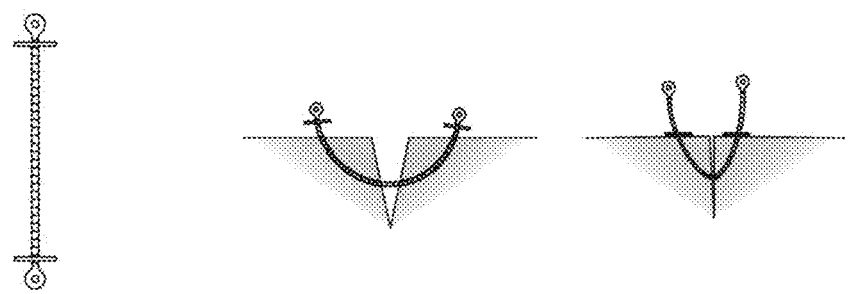
Fig. 33     (a)     (b)     (c)
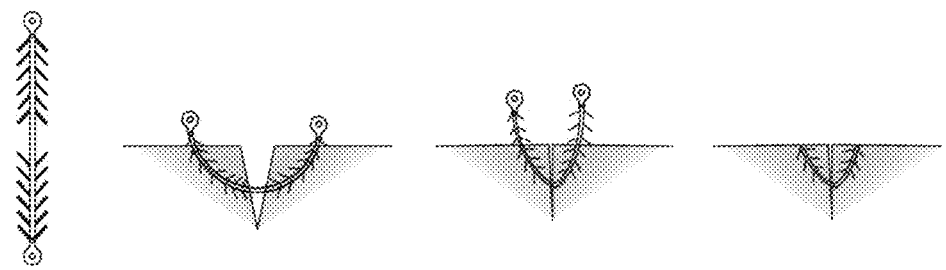
Fig. 34     (a)     (b)     (c)     (d)
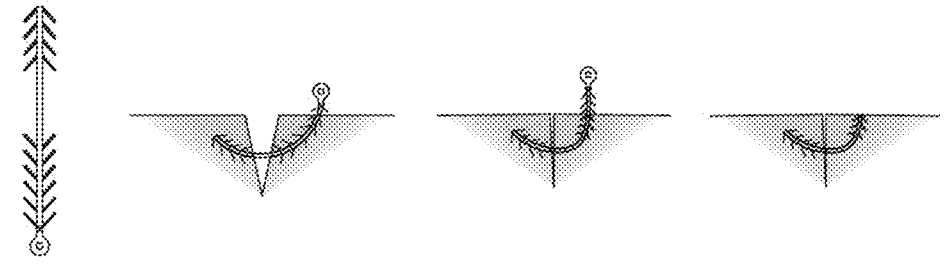
Fig. 35     (a)     (b)     (c)     (d)

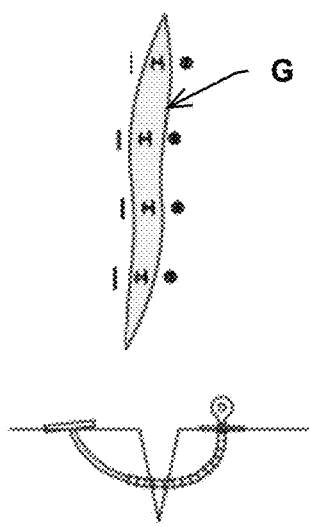
Fig. 36 (a)
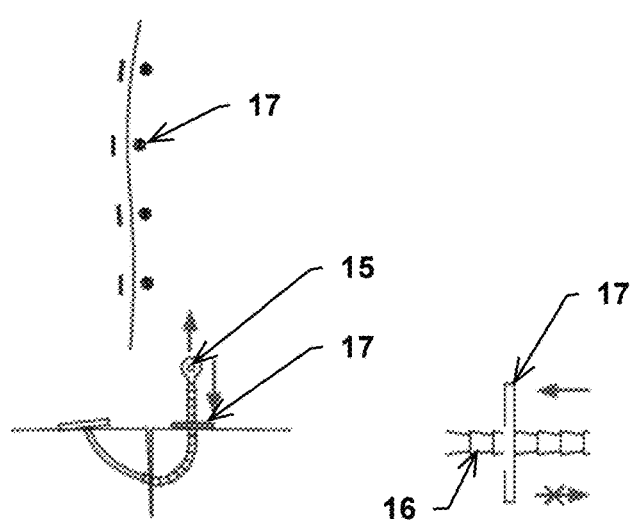
(b) Fig. 37
Fig. 38
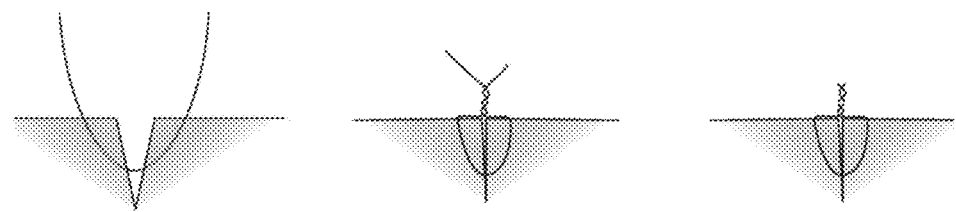
Fig. 39
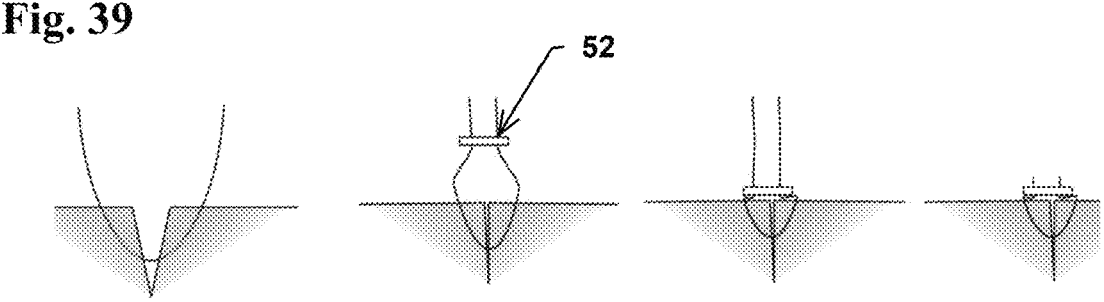
Fig. 40

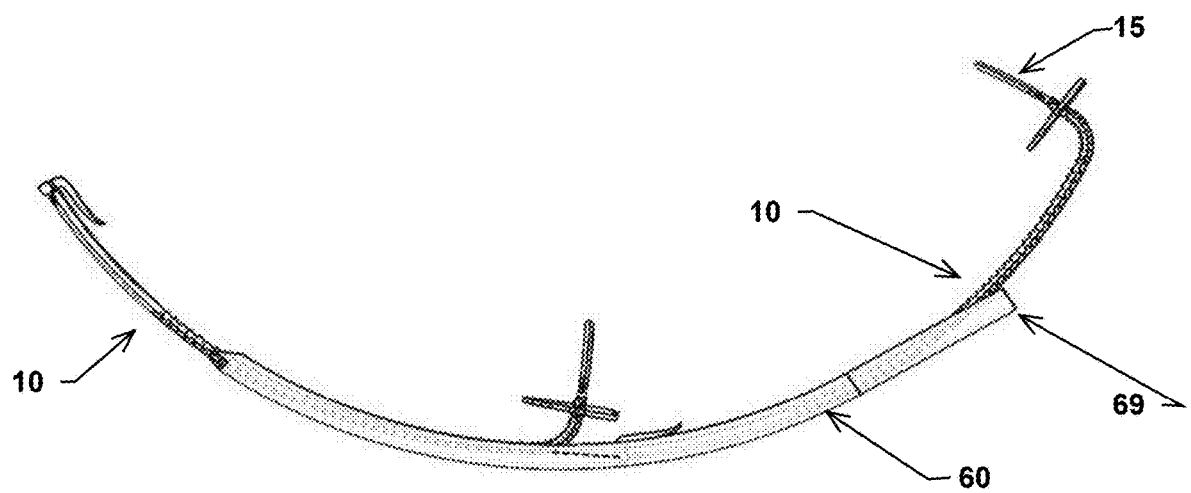
Fig. 45 (b)
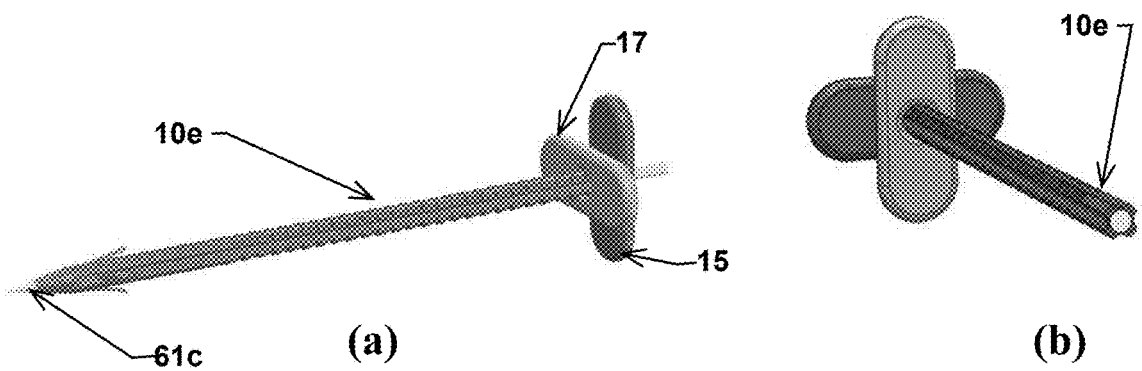
(a) (b)
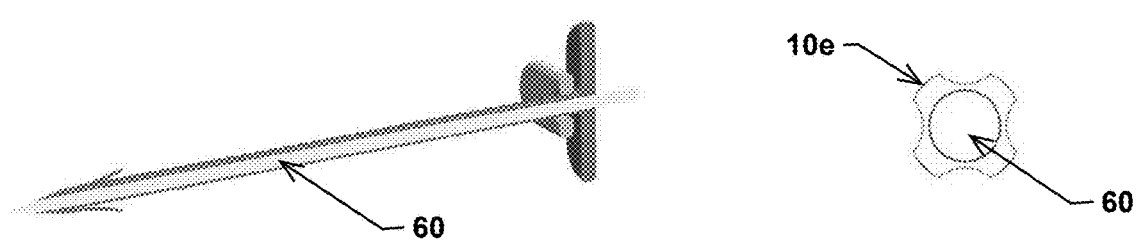
Fig. 46 (c) (d)

SUTURE MEMBER, SUTURING NEEDLE AND SUTURING DEVICE

TECHNICAL FIELD

The present invention relates to devices and systems for repairing human or animal soft tissue. More particularly, the invention concerns a surgical suture member, in particularly an interrupted suture member, a suturing needle for use with said suture member, and a suturing insertion apparatus for operating the suturing needle.

BACKGROUND

A surgical suture is used to hold body tissues together after injury or surgery. The sutures or stitches are typically applied using a needle with an attached piece of thread and are secured with surgical knots. The interrupted suture technique is the most commonly used technique in wound closure and is characterized in that individual stitches are not connected and each stich is secured by an individual knot. The process of making a knot for every stich is very time consuming.

The prior art includes CA 2 125 839 A1 (Feagin et al.), which discloses a soft tissue repair system and method, which includes a barbed suture anchoring member attached to at least one suture member. A suture retaining member engages the suture member such that the length and tension of the suture may be selectively adjusted before the suture is permanently engaged in the retaining member. In use, the barbed suture anchoring member and suture member are inserted into the soft tissue repair site and across a tear. The suture member extends back through the original entry side of the tear. A retaining member is applied to the suture member followed by tensioning of the suture member to draw the sides of the tear into apposition. Following tensioning, the retaining member is permanently affixed to the suture member to maintain the selected tension and length of the suture member.

The prior art also includes WO 2006/079469 A1 (Wohlert et al), which discloses a surgical suture system having a needle-like applicator with a tip in its front end area, with a surgical suture material provided with barbs which, on one side, preferably point in one direction of action from a reference point and, on the other side, point in the opposite direction of action from the reference point and are designed to block a movement of body tissue away from the reference point, and with a sheath whose front end area starts from the rear end area of the applicator and which surrounds the surgical suture material.

The prior art also includes CA 2 661 709 A1 (Cohen), which discloses suture having a proximal end defining a first outer diameter and a distal end configured to accommodate the proximal end of the suture to form a closed loop stitch.

The prior art also includes WO 90/14795 A2 (Yoon), which discloses a suture device composed of bioabsorbable material having an elongate body member having a sharpened distal end for penetrating the tissues, and a means locking said suture device in the tissues, to prevent forward and backward movement, and a suture device made of bioabsorbable material, having a hinge-like hinge for folding a part distal at a precise location to juxtapose with a proximal portion allowing an adjustable lock.

Accordingly, there is still need to improve the interrupted suture technique.

SHORT SUMMARY

The invention solving the above mentioned problems is an interrupted set forth and characterized in the main claims, while the dependent claims describe other characteristics of the invention.

According to one aspect, the invention provides an interrupted suture member that can easily be fastened and tighten without the use of a knot thereby reducing the time to place each stich.

According to another aspect, the invention provides a combination of an interrupted suture and a needle wherein the suture can easily be combined with the surgical needle without swaging.

According to another aspect of the invention, it provides a suturing insertion apparatus that is easily manipulated.

According to yet another aspect, it provides a suturing insertion apparatus for performing interrupted suture stiches that function in an area with limited space, limited mobility and limited visualization.

BRIEF DESCRIPTION OF THE DRAWINGS

These and other characteristics of the invention will become clear from the following description of various embodiments of the invention, given as non-restrictive examples, with reference to the attached schematic drawings, wherein:

FIGS. 1a and 1b are a perspective view and a side view, respectively, of a suture member according to a first embodiment of the invention;

FIG. 2a is a side view of the first end of the suture member illustrated in FIGS. 1a,b, showing a detent in a deployed position, while FIGS. 2b and 2c show the detent in folded, retracted, positions; FIGS. 2d to 2f are detailed perspective views of alternative embodiments of the detent of the invented suture member;

FIG. 3a is a side view of the first end of an embodiment of the invented suture member, and shows an alternative embodiment of a detent in a deployed position, while FIG. 3b shows the detent in a retracted position, wrapped around the a stem portion of the suture member;

FIGS. 4a-d are side views of alternative embodiments of the second end of the invented interrupted suture member;

FIGS. 5a,b are end views of alternative embodiments of a movable locking member arranged on the second end of the invented interrupted suture member;

FIGS. 6a-c are side views of alternative embodiments of a movable locking member arranged on the second end of the invented interrupted suture member;

FIG. 7 is a side view of a portion of the invented interrupted suture member, illustrating a method of manufacturing the movable locking member and the suture member stem;

FIG. 9 is a perspective view, illustrating alternative embodiments of the invented suture member;

FIG. 10 is a perspective view of a suturing apparatus according to an embodiment of the invention;

FIG. 11 is an enlarged view of the area marked "A" in FIG. 10;

FIG. 14a is a perspective view of a portion of a handle unit, and figure b is a perspective view of an embodiment of the suturing apparatus, schematically illustrating a driving connection interface between the handle unit and the suturing apparatus;

FIG. 15 is a perspective view of an assembled handle unit and suturing apparatus, performing a suturing procedure;

FIG. 16 is a schematic side view of a plurality of suturing apparatus arranged in a rack, and a handle unit configured for connection to the suturing apparatuses;

FIG. 17 is a perspective view of a plurality of interrupted suture members, arranged in a clip to be inserted into a suturing apparatus;

FIG. 18 is a schematic side view of a mechanically operated, unitized handle unit and suturing apparatus;

FIG. 21 is a side view of a suturing needle according to an embodiment of the invention, including enlarged views of both ends of the needle;

FIG. 22 is a side view of a suturing needle according to another embodiment of the invention, also showing a cross-section of a portion of the needle;

FIG. 23 is a side view of a suturing needle according to yet another embodiment of the invention;

FIGS. 24a-c illustrate various suturing needle cross-sections, 24a illustrates needle being solid, 24b illustrates a needle being hollow and 24c illustrates a needle being hollow with a slit;

FIG. 25 a-b are perspective views of alternative suturing needles according further embodiments of the invention;

FIG. 26 is a perspective view of a suturing needle according to yet another embodiment of the invention, also showing a top view of the needle and an exploded view of the tip end;

FIG. 28 illustrates a sequence of inserting a suturing needle of a first embodiment of the invention, into soft tissue;

FIG. 29 illustrates a sequence of inserting a suturing needle of a second embodiment of the invention, into soft tissue;

FIG. 30 illustrates a sequence of inserting a suturing needle into soft tissue, wherein the suturing needle subsequently is retracted;

FIG. 31a is a side view of an embodiment of the invented interrupted suture member, and FIGS. 31b,c illustrate a sequence of closing a gap in soft tissue by means of the suture member;

FIG. 32a is a side view of an embodiment of the invented interrupted suture member, and FIG. 32b illustrates the suture member installed in preparation to close a gap in soft tissue;

FIG. 33a is a side view of an embodiment of the invented interrupted suture member, and FIGS. 33b,c illustrate a sequence of closing a gap in soft tissue by means of the suture member;

FIG. 34a is a side view of an embodiment of the invented interrupted suture member, and FIGS. 34b-d illustrate a sequence of closing a gap in soft tissue by means of the suture member;

FIG. 35a is a side view of an embodiment of the invented interrupted suture member, and FIGS. 35b-d illustrate a sequence of closing a gap in soft tissue by means of the suture member;

FIG. 36a illustrates a plurality of an embodiment of the invented interrupted suture member, in plan view and section view, installed in soft tissue prior to closing a gap, and FIG. 36b illustrates, in plan view and section view, that the gap has been closed by activation of the movable locking member;

FIG. 37 is a side view of a portion of an embodiment of the invented interrupted suture member, illustrating the unidirectional movement of the movable locking member;

FIGS. 38, 39 and 40 illustrate sequences for closing a gap in soft tissue by means of alternative locking devices, techniques and member;

FIG. 43 is a side view sketch of yet an alternative suturing insertion apparatus, wherein the apparatus in manually operated and configured for inserting one interrupted suture member at a time into the tissue or manually operated and configured for inserting more than one suture member at the time wherein the different suture members are connected head to tail as illustrated in FIG. 46a;

FIGS. 46a-d illustrate an interrupted suture and needle combination according to an alternative embodiment of the invention wherein the needle is mounted inside a hollow interrupted suture and wherein the tip end of the needle is protruding out of the tip portion of the suture. FIGS. 46a and b are perspective views of the suture and needle combination and FIGS. 46c and d are cross-section views of the same suture-needle combination. The suture needle is solid as illustrated in FIG. 46d and FIG. 24a FIGS. 47a-c are perspective views of alternative interrupted sutures and needle combinations according to alternative embodiments of the invention wherein the tip portion of the needle has a notch further comprising a hole for catching and holding a tip portion of a suture member in place during insertion of the needle into the skin.

EMBODIMENTS OF THE INVENTION

Figure 8:
FIGS. 8a-e are side views and FIG. 8f is a perspective view illustrating alternative embodiments of the invented interrupted suture member.
Figure 8:
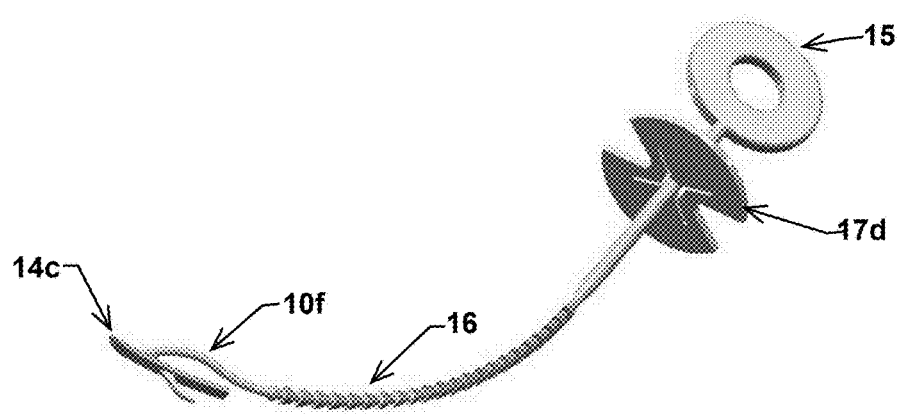
Figure 12:
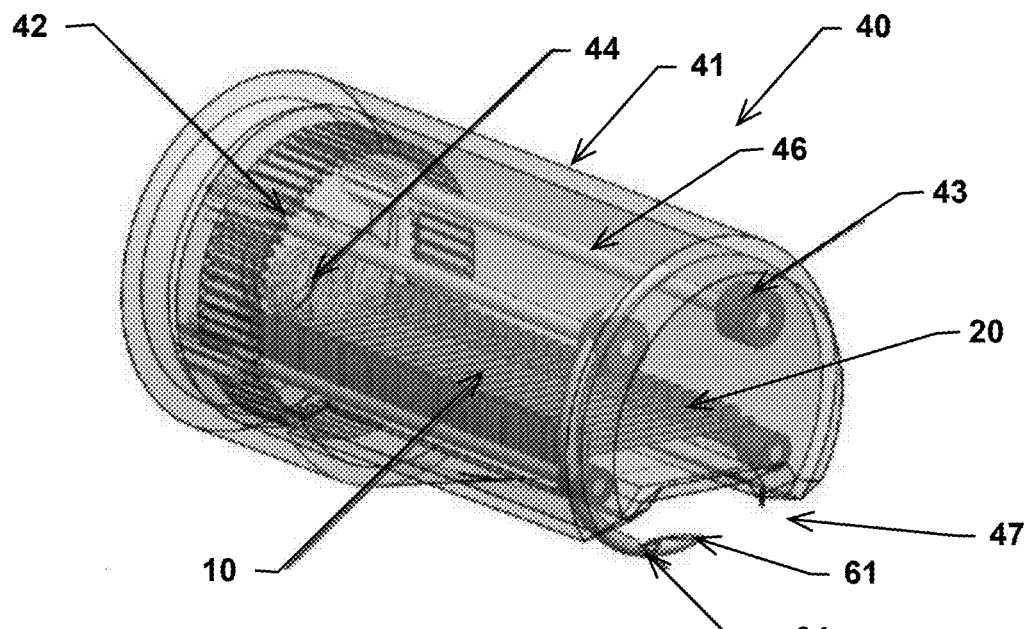
FIG. 12 is a perspective, transparent, view of a suturing apparatus according to an embodiment of the invention.
Figure 13:
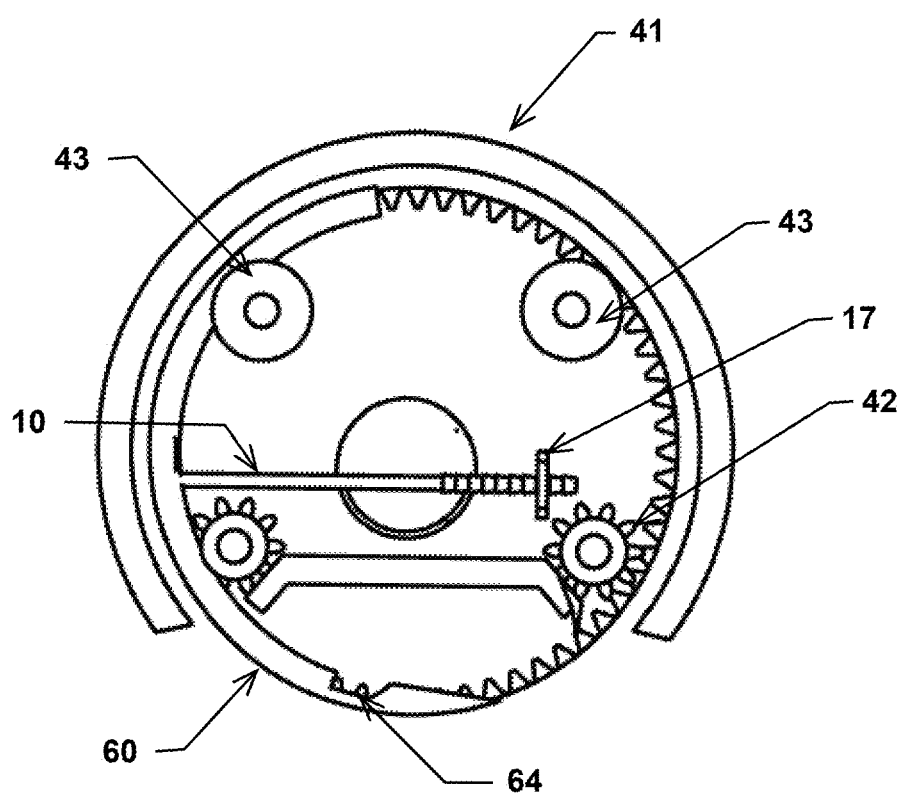
FIG. 13 is an axial view, as seen from a first end, of the suturing apparatus illustrated in FIGS. 10 and 12.

In the following description, various examples and embodiments of the invention are set forth in order to provide the skilled person with a more thorough understanding of the invention. The specific details described in the context of the various embodiments and with reference to the attached drawings are not intended to be construed as limitations. Rather, the scope of the invention is defined in the appended claims.

The following description may use terms such as "horizontal", "vertical", "lateral", "back and forth", "up and down", "upper", "lower", "inner", "outer", "forward", "rear", etc. These terms generally refer to the views and orientations as shown in the drawings and that are associated with a normal use of the invention. The terms are used for the reader's convenience only and shall not be limiting.

Moreover, the term "tissue" includes, but is not limited to, tissues such as skin, fat, fascia, bone, muscle, organs, nerves, or blood vessels or fibrous tissues such as tendons or ligaments.

The term "interrupted suture" is a suture according to the enclosed drawings of FIGS. 1 to 9 and wherein the suture is suitable for use in a suturing technique wherein individual stitches are not connected. The simple interrupted stich is a suturing technique often used to close wounds and is the most commonly used technique in the closure of skin.

The embodiments described below are numbered. In addition, dependent embodiments defined in relation to the numbered embodiments are described. Unless otherwise specified, any embodiment that can be combined with one or more numbered embodiments may also be combined directly with any of the dependent embodiments of the numbered embodiment(s) referred to.

In a first embodiment of the invention is an interrupted suture member-needle combination for connecting human or animal tissue comprising
 a) interrupted suture member (10) comprises a flexible elongate member (11), having a proximal tip (12) end and an distal end (13); wherein in that the tip end comprises two or more anchoring detents (14, 14a, 14b, 14c, 14d) configured for anchor the suture member in soft tissue, and in that the second end comprises a movable locking member (17, 17a, 17b, 17c, 17d, 17e) whereby a force exerted on the tissue by the detent and locking member may be adjusted by moving the locking member along at least a portion of the suture member, and
 b) a suture needle comprising a straight or arcuated body and a having a tip portion (61, 61a, 61b, 61c) further comprising a sharp cutting edge (63).

In a first related embodiment, the suture member is composed of a biocompatible such as serializable medical graded plastic material, polypropylene, polyester or polyamide.

In a related embodiment the suture member may have a stem (11) comprises ratchet means (16) on the entire stem or at least part of the stem.

In a related embodiment the suture may have at the head portion (13) a gripping portion shaped to be held and pulled by the user.

In a related embodiment the suture may comprise on one of the detents a notch suitable for holding the interrupted suture member in position in the needle during insertion of the suture member into the tissue.

In an alternative embodiment two or more suture members may be connected in a head-to-tail configuration.

In an alternative embodiment the needle may be hollow and having a slit sufficiently long and wide OR needle has a slit along the total length or at least part of the total length of the needle for easily insertion of the suture into the needle and for guiding the suture into the tissue.

In an alternative embodiment the tip portion of the needle may have a structure comprising two or more valleys for holding the suture anchor and two or more ridges wherein the ridges have sharp cutting edges for optimal skin penetration.

In an alternative embodiment the suture may have an anchoring structure with two detents.

In an alternative embodiment the needle may comprises a cutting edge (63) at the tip portion (61) and wherein the tail portion (69) of the needle has a notch (62) for catching and holding the suture at the detents of the structure of the suture for pulling the suture member into the tissue.

In an alternative embodiment the needle may comprises a notch (64) in the vicinity of the tip (61), configured for catching and holding the suture at the detents of the anchoring structure of the suture and push it into the tissue.

In an alternative embodiment suture anchoring structure may have a T-shape and wherein the anchoring structure further comprises a protrusion wherein said T-shape anchoring structure comprising said further protrusion is constructed to fit into said needle comprising the notch wherein the notch further comprises a hole for fitting the protrusion of the suture.

In an alternative embodiment one of the detents of the anchoring structure may be constructed to fit into said needle comprising the notch wherein the notch further comprises a hole for fitting the protrusion of the suture.

In a second embodiment of the invention is an interrupted suture member-needle combination for connecting human or animal tissue comprising
 a) interrupted suture member (10) comprises a flexible elongate member (11), having a proximal tip (12) end and an distal end (13); wherein in that the tip end comprises two or more anchoring detents (14, 14a, 14b, 14c, 14d) configured for anchor the suture member in soft tissue, and in that the second end comprises a movable locking member (17, 17a, 17b, 17c, 17d, 17e) whereby a force exerted on the tissue by the detent and locking member may be adjusted by moving the locking member along at least a portion of the suture member,
 b) a suture needle comprising a straight or arcuated body and a having a tip portion (61, 61a, 61b, 61c) further comprising a sharp cutting edge (63) and
 wherein the suture member is hollow and structured to hold a suturing needle inside the suture body wherein the tip of the needle protrude out of the tip portion if the hollow suture.

In a third embodiment of the invention which may be combined with the any of the above described embodiments further comprising two handles (54) mounted at the end portion (69) of the needle for catching and holding suture needle by the user.

In a forth embodiment of the invention is a suturing apparatus comprising a interrupted suture member-needle combination wherein the needle is an arcuated suturing needle rotatably arranged in an apparatus housing, a cavity for holding a plurality of suture members according to the invention, and drive means to selectively rotate said suturing needle.

In a further embodiment the suturing apparatus comprise feeding means whereby the suture member may be moved into contact with at least a portion of said suturing needle.

In a further embodiment the suturing apparatus further comprising a handle portion for releasable connection to the apparatus housing.

1. The Suture Member

Various embodiments of the invented interrupted suture member will now be described, primarily with reference to FIGS. 1 to 9.

The invented suture member 10 comprises an elongate member having a stem 11 and first 12 and second 13 ends. The first end may also be referred to as a tip portion 12 and the second end may be referred to a head portion 13. As seen in i.e. FIGS. 1*a,b*, the tip portion forms a T-shape, formed by a bar member 14 arranged transversely to the stem. In the following, the bar member may also be referred to as a detent 14 or an anchor 14.

The suture member 10, which is intended to be inserted into soft human- or animal tissue, is composed of a flexible or semi-rigid material which is biocompatible and inherently sterile. A non-limiting example of materials comprise polypropylene, polyester, polyamide (nylon), polytetrafluoroethylene, polyetherester, sterilizable medical graded plastic material. The suture member 10 may be formed partly of bioabsorbable materials, including but not limited to polydioxanone, polyactide, polyglycolide, polycaprolactone, and copolymers thereof.

Figure 45:
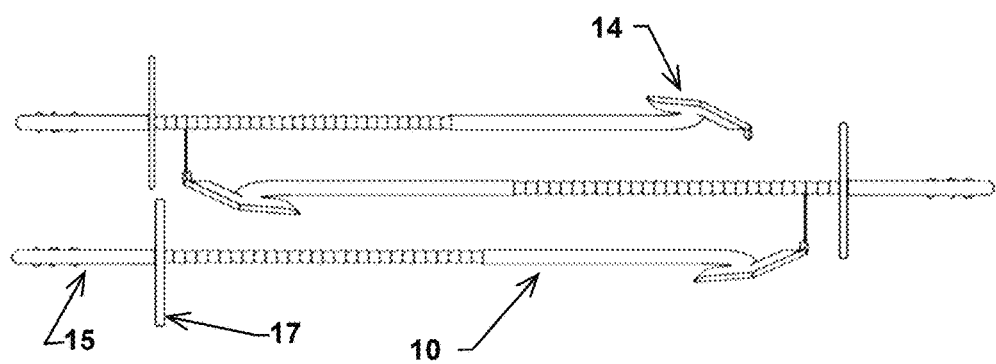
FIG. 45a is a side view of an alternative embodiment of the invention illustrating three interrupted suture members connected head-to-tail.
FIG. 45b is a side view of two consecutive interrupted sutures connected head-to-tail and in combination with a suture needle being hollow and having a slit according to the needles in FIGS. 24c and 27.

As will be explained later, the anchor 14 is retracted (i.e. folded or bent) during insertion of the suture member into the tissue. The suture member will thus move through the skin and dermis (penetrated by the suturing needle, described below) without causing excessive trauma. Examples of such retracted positions for the anchor are illustrated in FIGS. 2*b, c, d, e* and *f* while FIG. 2*a* illustrates a deployed position for the anchor. FIG. 2*d* illustrates an alternative embodiment of the anchor of FIGS. 2*a* and *b*, wherein the T-shape anchor of FIG. 2*d* has an additional notch 19 constructed to keep the anchor connected to a suturing needle tip 61 when the needle is penetrating the skin or tissue. FIG. 2*e* illustrates a further alternative embodiment of FIG. 2*c* in which the anchor has two or three detents or arms that are used to hold the suture in position in the needle during the penetration of the skin as exemplified in FIGS. 45 *b* and *c*. FIG. 2*f* illustrates a further alternative embodiment of the anchor in FIGS. 2*a* and *b* wherein the T-shape anchor has an additional protrusion A constructed to fit into a hole in a suture needle as exemplified in FIGS. 47*a* and *b*. The protrusion A is arranged at an acute angle pointing away from the needle tip 61 in order decrease the diameter of the needle and suture assembly. FIGS. 47*c* and *d* illustrates a further alternative embodiment of the anchor 14 wherein the anchor is formed as an arrow where the two detents forming the arrow head is arranged at acute angles in the direction away from the needle tip and one of the detents is constructed to fit into a hole in the suture needle. FIGS. 3*a,*3*b* illustrate an alternative embodiment of an anchor 14. In FIG. 3*b*, the anchor 14*d* is retracted, i.e. coiled around a portion of the stem 11, while FIG. 3*a* illustrates a deployed position. Once the suture member has been installed inside the tissue, the deployed anchor 14, 14*a*, 14*b*, 14*c* and 14*d* will be able to lock against tissue or skin.

The suture member second end, or head portion, 13 is in the embodiment shown in FIGS. 1*a,b* furnished with a gripping portion 15 with a hole in it. The gripping portion 15 is shaped to be held and pulled by a human user, in order to tighten the locking plate, as will be described later. The gripping portion 15, as well as any excess part of the stem, may be cut off once the suture member has been installed. FIG. 4*a* shows an embodiment with a head portion without any gripping portion. However, the head portion of this embodiment may be gripped and pulled by means of tweezers or other suitable instrument. FIG. 4*b* illustrates an embodiment having a cone-shaped gripping portion 15*a*. FIG. 4*c* illustrates an embodiment having a flat gripping portion 15*b*. FIG. 4*d* illustrates an embodiment having a flat, cone-shaped gripping portion 15*c*.

Referring again to FIGS. 1*a,b*, a movable locking member 17 is arranged around the stem 11 near the second end 13, and is configured to interact with ratchets 16 on the stem. This feature is illustrated in FIG. 37, and such unidirectional locking device is known in the art per se, although not applied to a suture member. The locking member 17 may thus be moved along the stem in a direction towards the first end 12, but not in the opposite direction. In FIGS. 5*a,b* and 6*a,b*, alternative embodiments of such movable locking members 17*a-d* are illustrated. FIG. 6*c* illustrates a different embodiment, in which the ratchets have been replaced by a thread 16*a*, and the movable locking member 17*e* is also threaded. The movable locking member 17*e* may thus be moved back and forth along the threaded portion of the stem 11.

The complete suture member 10, including the movable locking member, may be made (e.g. molded) in one piece, in a manner which per se is known in the art. The suture member may e.g. be molded with a fissure 18 (or weak zone) as shown in FIG. 7, and the locking member may subsequently separate along this fissure, whereupon it may be movable along the stem 11.

It should be understood that the suture member 10 illustrated in FIGS. 1*a,b* is merely one example of possible embodiments. For example, the entire stem 11 of the suture member 10*a* may comprise ratchet means (FIG. 8*a*), or the suture member 10*b* tip portion 12 may comprise one or more detents 14*d* (e.g. several detents arranged at acute angles, as shown in FIG. 8*b*). The suture member 10*c* may also have a symmetric configuration, in that gripping portion 15 and locking member 17 are arranged at opposite ends of the suture member (FIG. 8*c*). The stem of the suture member 10*d* may comprise ratchets means only at the head portion, as shown in FIGS. 8*b*, 8*d* and 8*e*. Referring to FIG. 9, the suture member 10*e* need not necessarily have a circular cross-section, but may have a rectangular cross-section (e.g. with ratchets 16*b* on opposite sides of step and a rectangular locking member 17*e*), or any other cross-sectional shape. The locking member 17 may also have a notch as illustrated in FIG. 8*f*.

It should be understood that these various features may be used interchangeably, depending on the specific application of the suture member. A common key feature, however, is the locking/tightening mechanism embodied by the movable locking member 17, whereby the suture member may be installed and re-tightened if need be.

2. The Suturing Apparatus

Various embodiments of the invented suturing apparatus will now be described, primarily with reference to FIGS. 10 to 20.

The suturing apparatus and clip-on cartridge 40 comprises in the embodiment illustrated in FIGS. 10-13, an outer housing 41 and a drive unit 42. A clip 20 (see also FIG. 17) holding a plurality of suture members 10 (in principle any one of the embodiments described above) is arranged inside the housing and is biased by a spring member 44 (FIG. 12), which will attempt to push the clip of suture members towards the housing opening 47. The drive unit 42 drives (via shafts 46) a plurality of capstans 43 arranged at or near the housing opening 47, where also a curved suturing needle 60 is arranged. The suturing needle 60 forms in the illustrated embodiment part of a circle, and is rotated by the capstans 43. The suturing needle 60 may thus be rotated around the suturing apparatus longitudinal axis by means of the drive unit and capstans.

As will de described in more detail below, the suturing needle suitable for use with the above describe apparatus comprises a notch 64, in the illustrated embodiment near the needle tip 61. Thus, in operation, the notch 64 in the rotating needle will catch the detent (or anchor) 14; 14c on a suture member 10 being pushed towards the opening 47, and pull the suture member out of its clip (and into tissues, as will be described below).

It should be understood that other means than those described and illustrated may be used to rotate the suturing needle. The apparatus may be configured and operated to make the needle rotate (i.e. complete revolutions), or move back and forth along its circular path.

It should also be understood that the drive unit may be powered by any known and suitable power source, such as a pneumatic device or an electric motor (not shown). The electric motor may be battery powered or comprise a cable for connection to an electric grid. In one embodiment, the power source may be housed in a separate, detachable, units, such as a handle unit 45, see FIGS. 14 and 15.

FIGS. 14a,b illustrate a driving connection interface between a handle unit 45 and the suturing apparatus 40. Switches, pushbuttons, etc. necessary to operate and control the suturing apparatus, are not illustrated as these are well known in the art.

Referring to FIG. 16, this modularized design allows the user to store several suturing clip-on cartridge 40, for example in a rack 48. The suturing apparatuses may be disposable, while the handle (including the power unit) may be reused.

In another embodiment, illustrated in FIG. 18, the handle unit 45 and suturing clip-on cartridge 40 may be formed as one integral unit, and for example be mechanically operated via a trigger 49.

Figure 19:
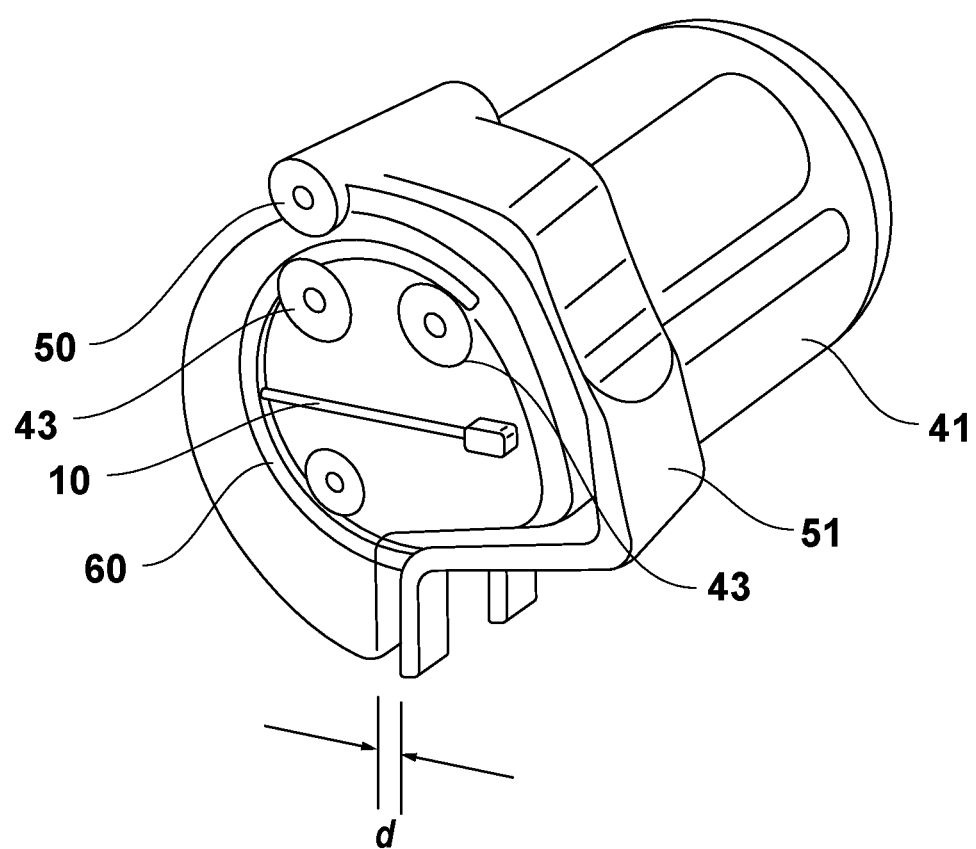
FIG. 19 is a perspective sketch of an embodiment of the suturing apparatus.
Figure 20:
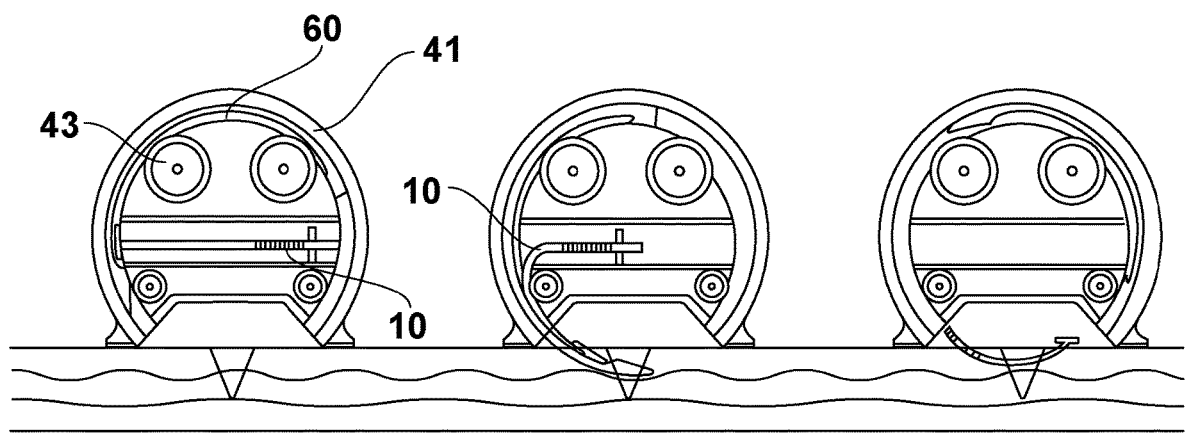
FIG. 20 is an illustration of the operation of an embodiment of the suturing apparatus, showing three stages of a suturing procedure.

FIG. 19 illustrates an embodiment of the suturing apparatus having a gap closing device 51 which is connected to the housing 41 via a hinge or other flexible joint 50. In an inactivated state a distance d is formed between the gap closing device 51 and a portion of the housing, this distance exceeding the tissue gap to be closed. In use, therefore, the housing is placed on the gap or scar to be sutured, and the gap closing device 51 is pressed towards the housing (reducing the distance d) and thereby pinching the skin to hold the gap in a closed state while the suturing procedure is ongoing.

3. The Suturing Needle

Various embodiments of the invented suturing needle 60 will now be described, primarily with reference to FIGS. 21 to 27. The embodiment of the needle 60 comprise an arcuate needle with a tip 61 is shown in FIGS. 21 to 23 and 25. The tip 61 may have a sharp cutting edge 63 for optimal skin penetration. The embodiment of the needle illustrated in FIG. 21 and FIG. 22 both comprise a notch 62 at the opposite end of the tip, configured for catching the suture member and pull it out of the suturing device and into the tissue. It should be understood that the notch may be arranged elsewhere on the needle 60. The embodiment of the needle illustrated in FIG. 22 comprises additionally a cutting edge 65 on the outer convex curvature.

The embodiment of the needle illustrated in FIG. 23 and FIG. 25 comprises a notch 64 in the vicinity of the tip, configured for catching the suture member and push it out of the suturing device and into the tissue. The embodiments of the needles illustrated in FIGS. 25 a and b further comprises a hole 64a for holding the suture when the needle is penetrating the skin. The embodiment showing the needle and suture combination is further illustrated in FIG. 47. The needle in FIG. 25b has a notch 64 wherein the notch has a slope or inclining angle towards the hole 64a.

It should be understood that the needle may be straight or curved and that the needle cross-section, completely or partly, may be solid, hollow, or hollow with a slit 66, as shown in FIGS. 24a-c, respectively.

Figure 27:
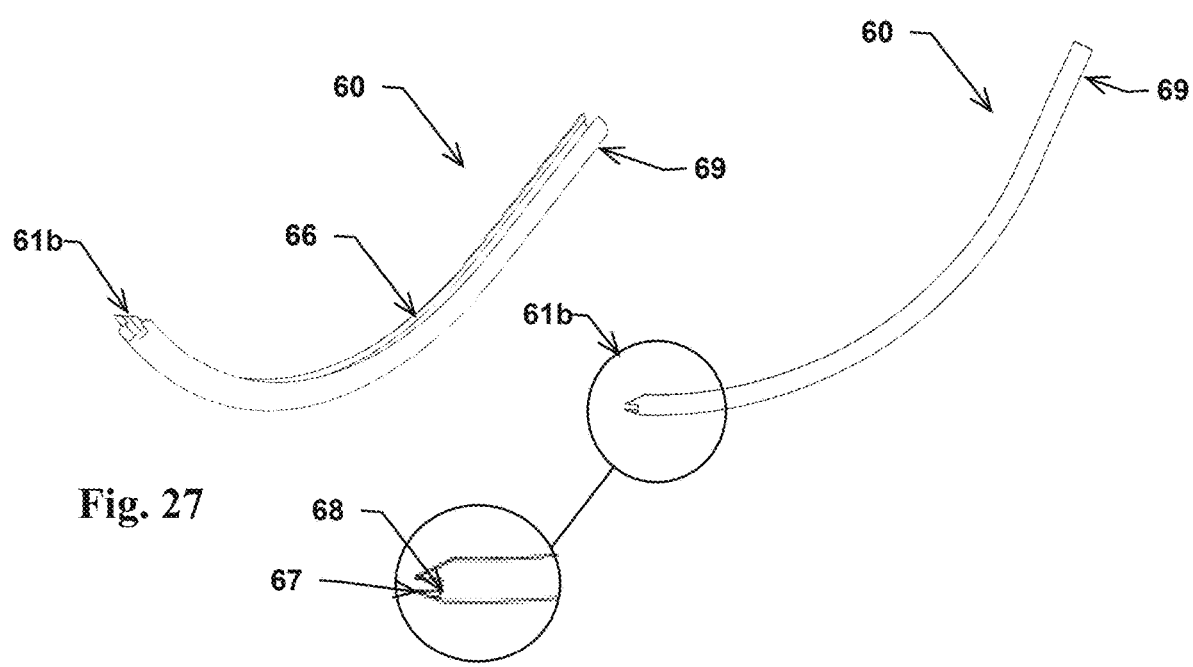
FIG. 27 is a perspective view of a suturing needle according to yet another embodiment of the invention, also showing a bottom perspective view of the needle and an exploded view of the tip end.

The embodiments of hollow needles are illustrated in FIGS. 26 and 27 comprising a slit 66 along the total length or at least part of the total length of the needle and having a tip 61a or 61b. The tip 61a or 61b includes a holding structure consisting of valleys between ridges for holding the suture member. The ridges comprise sharp cutting edges 63a for optimal skin penetration. The embodiment of the needle tip in FIG. 26 comprises two valleys 67 and three ridges 68 for holding the anchor structure suture in FIG. 8e having three arms. The embodiment of the needle tip in FIG. 27 comprises one valley 67 between two ridges 68 for holding the T-shape structure suture in FIG. 8d having two arms and a notch. The number of ridges and valleys on the needle tip can vary according to the invention and depends on structure and number of detents on the anchoring structure.

4. Methods of Operating the Inventions

Various uses of the inventions will now be described, primarily with reference to FIGS. 28 to 40.

FIG. 28 illustrates a sequence of inserting a suturing needle 60 having a notch near the back end of the needle (cf. FIG. 21 or 22), i.e. by pulling the suture member 10 out of the suturing apparatus (not shown in FIG. 28) and into the soft tissue T to close a gap G. The figure also indicates how the needle 60 completes a full revolution, and is arranged to catch the next suture member in the clip once a revolution has been completed.

FIG. 29 illustrates a sequence of inserting a suturing needle 60 having a notch near the tip of the needle (cf. FIG. 23), i.e. by pushing the suture member 10 out of the suturing apparatus (not shown in FIG. 26) and into the soft tissue T to close a gap G. The figure also indicates how the needle 60 completes a full revolution, and is arranged to catch the next suture member in the clip once a revolution has been completed.

FIG. 30 illustrates a sequence of inserting a suturing needle into soft tissue, wherein the suturing needle does not complete a full revolution, but is retracted (as indicated by the arrows) once the suture member has been placed in the tissue.

As mentioned above, the suture member is intended to be inserted into soft animal tissue T, and is formed of a flexible material which is bio-compatible and inherently sterile. The entire suture member, or parts of it, may be formed of an absorbable material.

In FIG. 31b, an embodiment of the invented suture member has been installed in the tissue, spanning the gap G. In FIG. 31c, the movable locking device has been moved along the suture member 10 to tighten the tissue and close the gap G. The detents 14d are in the deployed state and lodged inside the soft tissue T. A corresponding installation is illustrated in FIG. 32b, wherein the suture member has been installed in preparation to close the tissue gap.

FIGS. 33a to 35d illustrate other embodiments of the invented suture member, installed in tissue. FIG. 36a illustrates a plurality of suture members installed in soft tissue prior to closing a gap G, and FIG. 36b illustrates that the gap has been closed by activation of the movable locking members 17.

FIGS. 34, 35, 36, 38, 39 and 40 illustrate sequences for closing a gap in soft tissue by means of alternative locking devices, techniques and member. In FIG. 38 a variant of the suture member akin to a cable tie has been inserted into the tissue and subsequently tightened to close the tissue gap. In FIG. 39 a twistable variant of the suture member has been inserted into the tissue, and the ends twisted together to close the gap. In FIG. 40, a locking device 52 has been used to secure the suture member and to close the gap. It should be understood that these variants of the suture member may be installed by means of the suturing apparatus and needle described above.

5. Other Suturing Insertion Apparatuses

Figure 41:
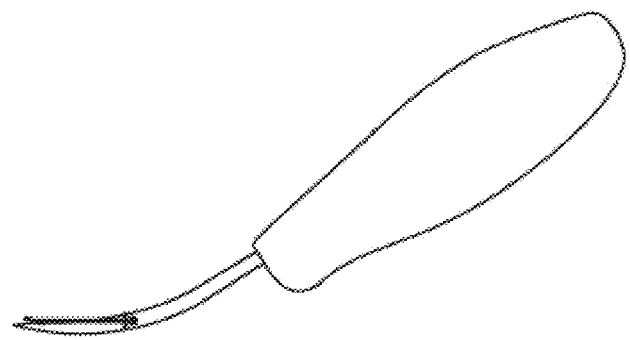
FIG. 41 is a side view sketch of an alternative suturing insertion apparatus, wherein the apparatus is manually operated and configured for inserting one interrupted suture member at a time into the tissue.

FIG. 41 illustrates an alternative embodiment of the suturing insertion apparatus, wherein the insertion apparatus is manually operated and configured for inserting one suture member at a time into the tissue.

Figure 42:
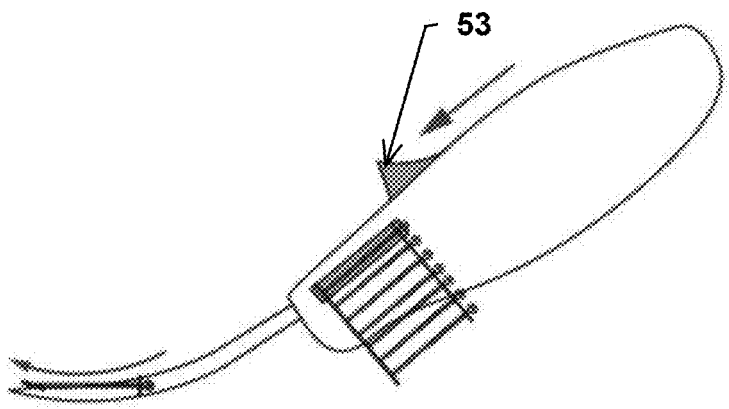
FIG. 42 is a side view sketch of yet an alternative suturing insertion apparatus, wherein the apparatus in manually operated and configured for connection to a clip of interrupted suture members.

FIG. 42 illustrates an alternative suturing insertion apparatus, in which the suture member is pushed through a hollow needle by an internal rod (nod shown) connected to a trigger 53 in the handle. A spring (not shown) will reset the trigger and rod, and pull the next suture member from the clip and into the tubular needle.

Figure 43:
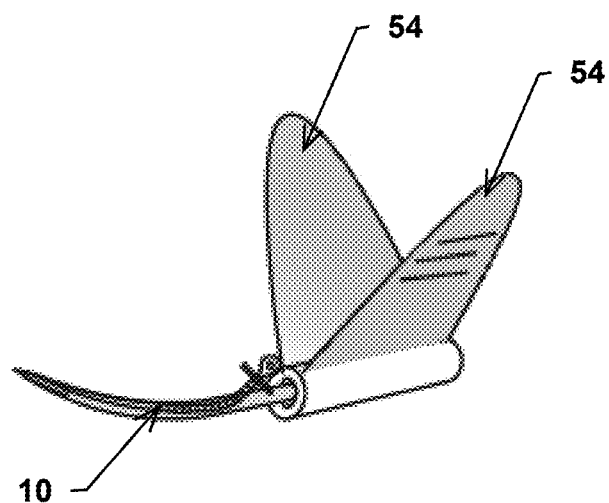

FIG. 43 illustrates an alternative suturing insertion apparatus, wherein the apparatus in manually operated and configured for inserting one suture member or more than one suture member (illustrated in FIG. 45) at a time into the tissue. A suture member 10 is placed in a hollow needle having a slit along the total length of the needle as further illustrated in FIG. 44. The apparatus is operated by the user holding two handles 54 and inserting the needle into the tissue. The two handles 54 are grabbed by the user and pushed together to get a good and easy grip when manipulating the suturing apparatus. When the needle is pulled out from the tissue, the suture member remains by virtue of its detents (or anchor).

6. Alternative Suture and Needle Combinations

Common feature of the alternative suture and needle shown in FIGS. 44 to 47 is that the anchor 14 at the tip portion 12 of the suture is constructed to fit a particular needle construction in order to ease the assembly of the suture and needle and also to decrease the diameter of the suture-needle combination.

Figure 44:
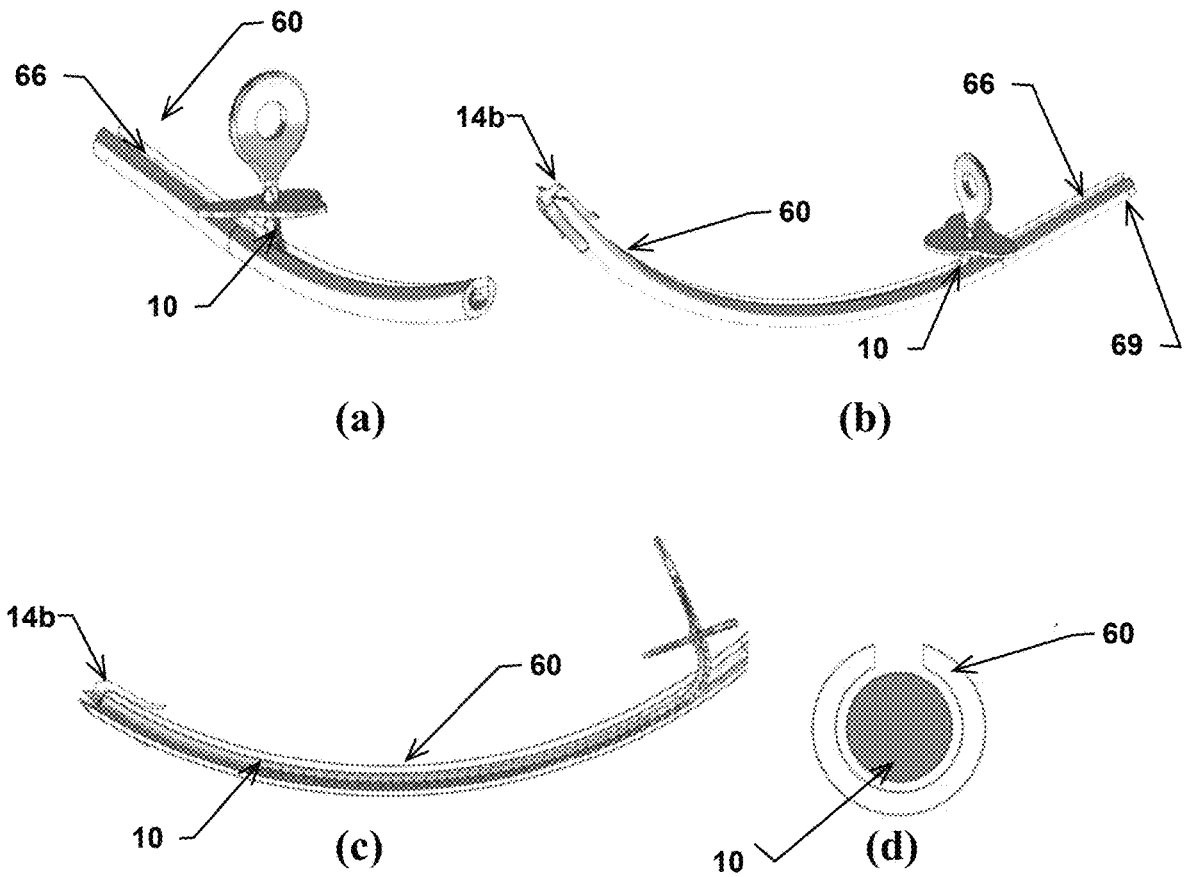
FIGS. 44a and b are perspective views of an alternative embodiment of the invention illustrating an interrupted suture in combination with a surgical needle wherein the needle is hollow and having a slit according to the needles in FIGS. 24c and 26, FIGS. 44c and d also showing two cross-section views of the suture and needle combination.

FIGS. 44 to 47 illustrates preferred combinations of interrupted sutures and needles. The suture and needle combinations shown in FIGS. 44 and 45 may be used with the suturing apparatus illustrated in FIG. 43. FIG. 44 illustrates an embodiment comprising a suture-needle combination, wherein the needle 60 is hollow and comprises a slit 66 along the total length or at least part of the total length of the needle. The slit may be used for easy insertion of the suture into the needle and for guiding the suture when the suture-needle combination is inserted into human or animal tissue. The needles in FIGS. 44 and 45 may further comprises two or more valleys 68 at the tip of the needle that together with the formed ridges 67 are engaged to hold the suture anchor in place during insertion of the needle into tissue. FIG. 45a illustrates an alternative embodiment where two or more interrupted sutures are connected head-to-tail for insertion of two or more consecutive sutures into the hollow needle having a slit 66, FIG. 45b.

FIG. 46 illustrates an alternative suture-needle combination wherein the suture 10e is hollow and encompasses a suture needle 60 wherein the tip end of the needle is protruding out of the tip portion of the suture and the tip portion of the suture comprises detents that are deployed when the suture is installed in the tissue.

Figure 47:
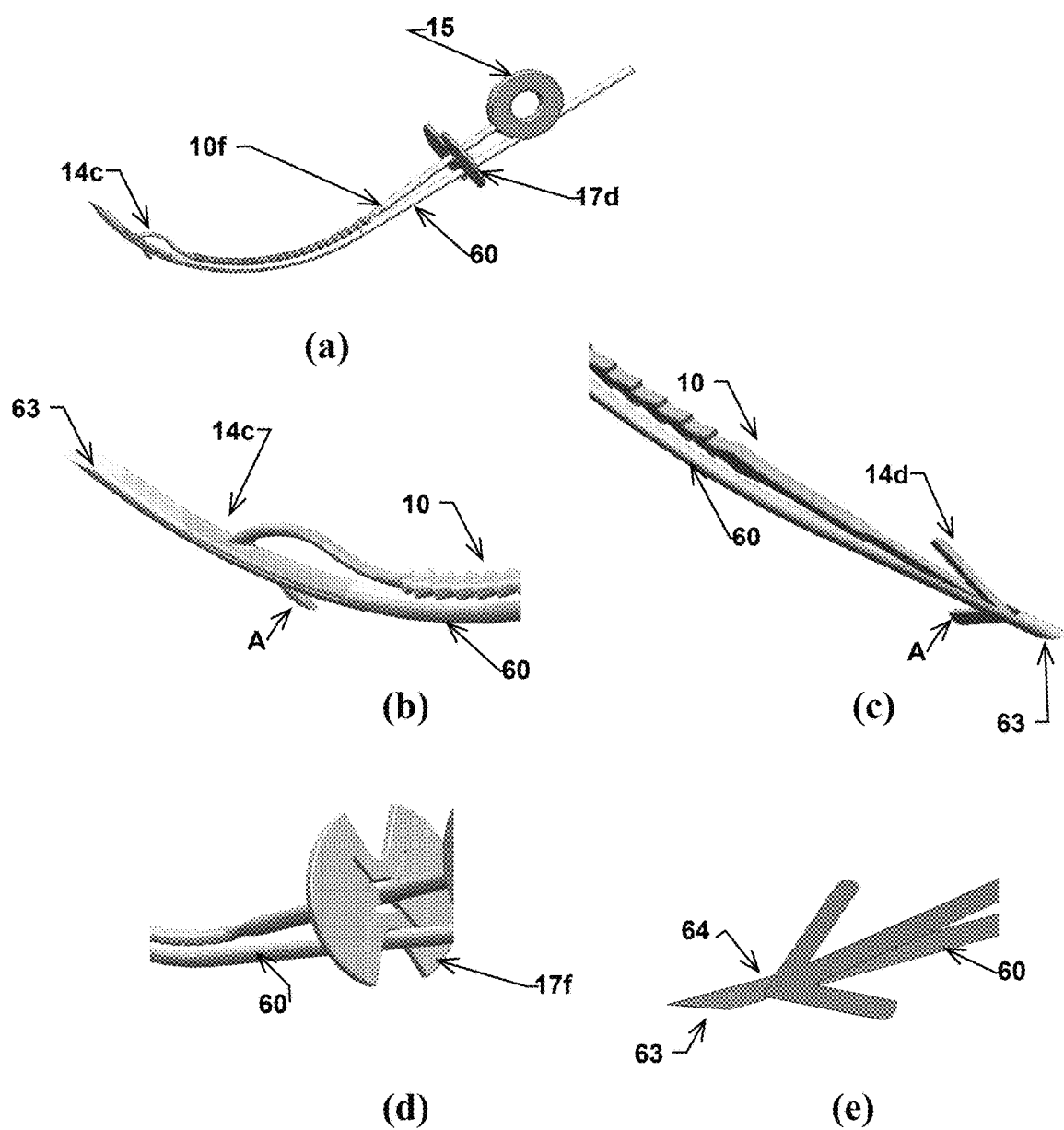
FIG. 47d illustrates part of the interrupted sutures and needle combination wherein the movable locking member has a notch for keeping the suture in place during insertion of the needle into the skin.
FIG. 47e is a cross section of the suture and needle combination in c.

FIG. 47 illustrates yet another interrupted suture-needle combination wherein the anchor 14 of the suture 10 is connected to the needle in a notch 64 situated in the tip portion of the needle during insertion of the needle into the tissue. This suture-needle combination may be used with the suturing apparatus as illustrated in FIGS. 10 to 20. The notch 64 in the tip portion of the needle further comprising a hole 64a for catching and holding the anchor 14 of the suture member in place during insertion of the needle into the skin. The movable locking member 17 may comprises a notch for holding and guiding the head portion of the suture to the needle upon insertion of the needle and suture into tissue, 47d. FIGS. 47c and d illustrates an alternative embodiment of the suture-needle combination in FIGS. 47a and b wherein the suture may have an anchor 14 formed as an arrow wherein one of the detents of the arrow is constructed to fit into the hole 64a of the needle in order to keep the suture attached to the needle during insertion into the tissue.

Figure 48:
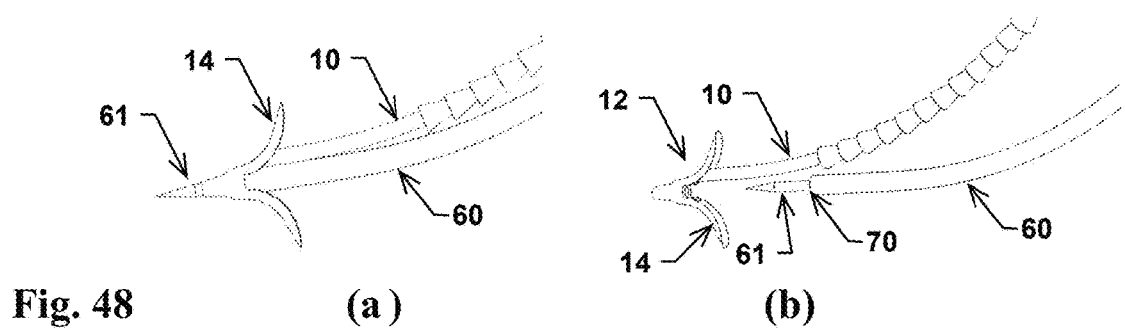
FIGS. 48a-b are perspective views of an interrupted suture member-needle combination according to an embodiment of the invention.

FIGS. 48a and 48b illustrate yet another interrupted suture member-needle combination comprising a suture member 10 and a suture needle 60. In FIG. 48a, the interrupted suture member 10 and suture needle 60 are assembled, and in FIG. 48b the interrupted suture member 10 and suture needle 60 are disassembled for illustrating purposes. The suture member 10 comprises a proximal tip 12 and an anchor 14. The suture needle 60 comprises a tip 61. The tip 61 is configured for insertion through the proximal tip 12, but the suture needle 60 is restricted from extending through the proximal tip 12. A stopping element 70 may restrict the suture needle 60 from extending through the proximal tip 12. The stopping element 70 may be a step, a protrusion, an increase in thickness of a part of the body of the needle 70, etc.

In the exemplary embodiments, various features and details are shown in combination. The fact that several features are described with respect to a particular example should not be construed as implying that those features by necessity have to be included together in all embodiments of the invention. Conversely, features that are described with reference to different embodiments should not be construed as mutually exclusive. As those with skill in the art will readily understand, embodiments that incorporate any subset of features described herein and that are not expressly interdependent have been contemplated by the inventor and are part of the intended disclosure. However, explicit description of all such embodiments would not contribute to the understanding of the principles of the invention, and consequently some permutations of features have been omitted for the sake of simplicity or brevity.

LIST OF REFERENCE SIGNS

10 Suture member
11 Stem
12 First end or tip portion or proximal end
13 Second end or head portion or distal end
14 Anchor
15 Gripping portion
16 Ratchets
17 Movable locking member
18 Fissure 19 Notch
20 Magazine
40 Clip-on cartridges
41 Outer housing
42 Drive unit
43 Capstans
45 Handle unit
47 Housing opening
48 Rack
49 Trigger
50 Hinge or flexible joint
51 Gap closing device
52 Locking device
53 Trigger
54 Handles
60 Suturing needle
61 Tip or head portion
62 Notch back end of the needle
63 Cutting edge
64 Notch near the tip end
64a Slot
65 Cutting edge
66 Slit
67 Ridges
68 Valley
69 Tail portion, end portion
70 Stopping element

The invention claimed is:

1. An interrupted suture member-needle combination for connecting human or animal tissue comprising
   a) the interrupted suture member comprises a flexible elongate member comprising a plurality of indents, ridges or locking teeth arranged along a portion of the elongate member, having a distal tip end and a proximal end, wherein the distal tip end comprises two or more anchoring detents configured for anchoring the interrupted suture member in tissue and defining a channel, wherein the channel is a through-hole extending through the distal tip end between the anchoring detents and the proximal end comprises a movable locking member arranged around the elongate member and wherein the locking member comprises resilient locking arm for locking engagement with the plurality of indents, ridges or locking teeth of the elongate member, the locking member further comprising a tissue abutment surface having a larger cross section than the interrupted suture member adapted to abut the tissue and whereby a force exerted on the tissue by the anchoring detents and the locking member may be adjusted by moving the locking member along at least a portion of the interrupted suture member and wherein the locking member is adapted to move towards the distal tip end and not in the opposite direction, and
   b) the suture needle comprising a straight or arcuated body having a tip portion and an end portion, the tip portion further comprises a sharp cutting edge wherein the tip portion is configured for insertion through the channel in the distal tip end of the interrupted suture member and wherein the suture needle is restricted from extending through the distal tip end of the interrupted suture member by a stopping element wherein the stopping element comprises a step, a protrusion or an increase in thickness of a part of the body of the needle for interactions with the sides of the channel.

2. The interrupted suture member-needle combination of claim 1, wherein the interrupted suture member is composed of a biocompatible material such as sterilisable medical graded plastic material, polypropylene, polyester or polyamide.

3. The interrupted suture member-needle combination of claim 1, wherein the interrupted suture member comprises a stem comprising the plurality of indents, ridges or locking teeth on the entire stem or only at part of the of the stem.

4. The interrupted suture member-needle combination of claim 1, wherein the proximal end of the interrupted suture member has a gripping portion shaped to be held and pulled by the user.

5. The interrupted suture member-needle combination of claim 1 further comprising two handles mounted at the end portion of the needle for catching and holding the suture needle by the user.

6. An interrupted suture device comprising
   a flexible, elongate member having a distal end and a proximal end, with a plurality of indents, ridges or locking teeth arranged along a portion of the elongate member,
   a tissue insertion tip arranged for facilitating a one-way insertion of the distal end of the elongate member through human or animal tissue, the tissue insertion tip comprising
   a throughgoing channel portion arranged to receive a cutting end of a suture needle, a length of the channel selected such that a portion of the cutting end of the suture needle protrudes past the throughgoing channel portion,
   the throughgoing channel portion displaying a cross-section that is smaller than a step, protrusion or area of increased thickness of the suture needle, the throughgoing channel portion thereby being adapted for abutment with the step, protrusion or area of increased thickness of the suture needle when the suture needle is inserted therethrough
   such that a forward pressure of the suture needle against the tissue will cut the tissue and force the tissue insertion tip forward through the tissue when the suture needle is inserted into the throughgoing channel portion, and
   a flexible, resilient retraction-preventing detent arranged to compress as the tissue insertion tip is passed through the tissue and rebound to an extended position after insertion, thereby preventing retraction of the tissue insertion tip back though the tissue, and
   a movable locking member arranged at the proximal end of the elongate member, the locking member having resilient arms for locking engagement with the plurality of indents, ridges or locking teeth of the elongate member, the locking member further comprising a tissue abutment surface having a larger cross section than the elongate member for abutment against the tissue.

7. A suture system, comprising the interrupted suture device of claim 6, and a suture needle arranged to be functionally inserted into the throughgoing channel of the tissue insertion tip of the interrupted suture device.

8. A method of suturing a cut or wound in tissue, comprising,
   providing the interrupted suture device of claim 6,
   inserting a cutting end of a suture needle into the throughgoing channel of the tissue insertion tip of the suture device, such that the cutting end protrudes past the throughgoing channel,
   pressing the suture needle through the tissue at a location of the cut or wound, such that the tissue insertion tip passes through the tissue, and the resilient detents expand once the tissue insertion tip passes though the tissue, thereby preventing retraction of the tissue insertion tip through the tissue, pressing the locking member forward against the tissue with sufficient force to close the cut or wound, the resilient arms of the locking member engaging the indents, ridges or locking teeth of the elongate member of the interrupted suture device, thereby holding the tissue abutment surface of the locking member.

\* \* \* \* \*